United States Patent
Rodino-Klapac

(10) Patent No.: US 11,820,972 B2
(45) Date of Patent: Nov. 21, 2023

(54) METHODS OF TREATING MUSCULAR DYSTROPHY

(71) Applicant: RESEARCH INSTITUTE AT NATIONWIDE CHILDREN'S HOSPITAL, Columbus, OH (US)

(72) Inventor: Louise Rodino-Klapac, E. Groveport, OH (US)

(73) Assignee: RESEARCH INSTITUTE AT NATIONWIDE CHILDREN'S HOSPITAL, Columbus, OH (US)

( * ) Notice: Subject to any disclaimer, the term of this patent is extended or adjusted under 35 U.S.C. 154(b) by 401 days.

(21) Appl. No.: 15/775,566

(22) PCT Filed: Nov. 11, 2016

(86) PCT No.: PCT/US2016/061703
§ 371 (c)(1),
(2) Date: Dec. 26, 2018

(87) PCT Pub. No.: WO2017/083776
PCT Pub. Date: May 18, 2017

(65) Prior Publication Data
US 2018/0340187 A1 Nov. 29, 2018

Related U.S. Application Data

(60) Provisional application No. 62/419,793, filed on Nov. 9, 2016, provisional application No. 62/254,539, filed on Nov. 12, 2015.

(51) Int. Cl.
| | | |
|---|---|---|
| *C12N 15/85* | (2006.01) | |
| *A61K 48/00* | (2006.01) | |
| *A01K 67/027* | (2006.01) | |
| *C07K 14/705* | (2006.01) | |
| *C07K 14/47* | (2006.01) | |
| *C07K 14/435* | (2006.01) | |
| *C12N 15/86* | (2006.01) | |
| *A61P 21/00* | (2006.01) | |
| *A61K 31/122* | (2006.01) | |
| *A61K 31/355* | (2006.01) | |
| *A61K 45/06* | (2006.01) | |

(52) U.S. Cl.
CPC ...... *C12N 15/8509* (2013.01); *A01K 67/0276* (2013.01); *A61K 31/122* (2013.01); *A61K 31/355* (2013.01); *A61K 45/06* (2013.01); *A61K 48/005* (2013.01); *A61P 21/00* (2018.01); *C07K 14/435* (2013.01); *C07K 14/4707* (2013.01); *C07K 14/705* (2013.01); *C12N 15/86* (2013.01); *A01K 2217/075* (2013.01); *A01K 2227/105* (2013.01); *A01K 2267/0306* (2013.01); *C12N 2015/8518* (2013.01); *C12N 2015/8536* (2013.01); *C12N 2750/14143* (2013.01); *C12N 2830/008* (2013.01)

(58) Field of Classification Search
CPC .... A61K 48/00; C12N 15/8509; C12N 15/86; A01K 2267/0306
See application file for complete search history.

(56) References Cited

U.S. PATENT DOCUMENTS

| | | |
|---|---|---|
| 6,204,059 B1 | 3/2001 | Samulski et al. |
| 9,434,928 B2 | 9/2016 | Mendell et al. |
| 2010/0026655 A1 | 2/2010 | Harley |
| 2010/0120627 A1 | 5/2010 | Belouchi et al. |
| 2010/0266551 A1 | 10/2010 | Richard et al. |
| 2011/0082192 A1 | 4/2011 | Milne et al. |
| 2011/0266551 A1 | 11/2011 | Thompson et al. |
| 2014/0234255 A1 | 8/2014 | Lai et al. |
| 2014/0249208 A1 | 9/2014 | Bancel et al. |
| 2014/0323956 A1 | 10/2014 | Mendell et al. |
| 2015/0125429 A1 | 5/2015 | Perlingeiro et al. |

FOREIGN PATENT DOCUMENTS

| | | | |
|---|---|---|---|
| EP | 127839 A2 | 12/1984 | |
| EP | 155476 A1 | 9/1985 | |
| EP | 2170325 A2 | 4/2010 | |
| EP | 2859896 A1 * | 4/2015 | ........... A61K 31/221 |
| EP | 3030666 A1 | 6/2016 | |
| JP | 2006-121961 A | 5/2006 | |
| WO | WO-02/053703 A2 | 7/2002 | |
| WO | WO-03/074714 A1 | 9/2003 | |
| WO | WO-2013078316 A1 * | 5/2013 | ............. A61P 21/00 |
| WO | WO-2014/037526 A1 | 3/2014 | |

OTHER PUBLICATIONS

Grose (PLoS ONE, 7(6): e39233, 1-10, 2012) (Year: 2012).*
Bolduc (The American Journal of Human Genetics, 86: 213-221, 2010) (Year: 2010).*
Mahmood (Molecular Medicine Reports, 9: 1515-1532, 2014) (Year: 2014).*
Au (Front. Med. 8:809118, 2022) (Year: 2022).*
Mingozzi (Nature reviews Genetics, 12(341): 1-16, 2011) (Year: 2011).*
Xu (Skeletal Muscle (2015) 5:43) (Year: 2015).*
Thiruvengadam (Journal of Neuromuscular Diseases 8 (2021) S243-S255) (Year: 2021).*
Daya (Clin Microbiol Rev, 21(4): 583-593, 2008) (Year: 2008).*
Kennell, Progr Nucleic Acid Res. Mol. Biol. 11: 259-301, 1971, (Year: 1971).*
Abadi et al., Supplementation with alpha-lipoic acid, CoQ10, and vitamin E augments running performance and mitochondrial function in female mice, PLoS One, 8(4):e60722 (2013).

(Continued)

*Primary Examiner* — Valarie E Bertoglio
(74) *Attorney, Agent, or Firm* — MARSHALL, GERSTEIN & BORUN LLP

(57) ABSTRACT

The invention provides for AAV vectors expressing the ANO5 gene and antioxidant therapy as methods of inducing muscle regeneration and a method of treating muscular dystrophy.

9 Claims, 6 Drawing Sheets
Specification includes a Sequence Listing.

(56) References Cited

OTHER PUBLICATIONS

Anderson et al., Quantitative Filter Hybridisation, p. 73 (Chapter 4), IN: Hames et al. (eds.), Nucleic Acid Hybridisation: A Practical Approach, IRL Press Limited (1985).
Arnold et al., Electrophysiological Biomarkers in Spinal Muscular Atrophy: Preclinical Proof of Concept, Ann. Clin. Transl. Neurol., 1(1):34-44 (Jan. 2014).
Beastrom et al., mdx(5cv) mice manifest more severe muscle dysfunction and diaphragm force deficits than do mdx Mice, Am. J. Pathol., 179(5):2464-74 (Nov. 2011).
Bolduc et al., Recessive mutations in the putative calcium-activated chloride channel Anoctamin 5 cause proximal LGMD2L and distal MMD3 muscular dystrophies, Am. J. Hum. Genet., 86(2):213-21 (Feb. 2010).
Bouquet et al., Miyoshi-like distal myopathy with mutations in anoctamin 5 gene, Rev. Neurol. (Paris), 168(2):135-41 (Feb. 2012).
Chandrasekharan et al., Genetic defects in muscular dystrophy, Methods Enzymol. 479:291-322 (2010).
Chao et al., Several log increase in therapeutic transgene delivery by distinct adeno-associated viral serotype vectors, Mol. Ther. 2:619-23 (2000).
Chao et al., Sustained and complete phenotype correction of hemophilia B mice following intramuscular injection of AAV1 serotype vectors, Mol. Ther. 4:217-22 (2001).
Chiorini et al., Cloning and characterization of adeno-associated virus type 5, J. Virol., 73(2):1309-19 (Feb. 1999).
Chiorini et al., Cloning of adeno-associated virus type 4 (AAV4) and generation of recombinant AAV4 particles, J. Virol., 71(9):6823-33 (Sep. 1997).
Clark et al., Highly purified recombinant adeno-associated virus vectors are biologically active and free of detectable helper and wild-type viruses, Hum. Gene Ther., 10(6):1031-9 (Apr. 1999).
Clark et al., Recombinant adeno-associated viral vectors mediate long-term transgene expression in muscle, Hum. Gene. Ther. 8:659-69 (1997).
Cserjesi et al., Myogenin induces the myocyte-specific enhancer binding factor MEF-2 independently of other muscle-specific gene products, Mol. Cell. Biol., 11:4854-62 (1990).
De et al., High levels of persistent expression of alpha1-antitrypsin mediated by the nonhuman primate serotype rh. 10 adeno-associated virus despite preexisting immunity to common human adeno-associated viruses, Mol. Ther. 13:67-76 (2006).
European Patent Application No. 16865168.5, Communication Pursuant to Rule 164(1) EPC, dated Feb. 1, 2019.
Forbes et al., Skeletal muscles of ambulant children with Duchenne muscular dystrophy: validation of multicenter study of evaluation with MR imaging and MR spectroscopy, Radiology, 269(1):198-207 (2013).
Gao et al., Clades of Adeno-associated viruses are widely disseminated in human tissues, J. Virol. 78:6381-8 (2004).
Genbank Accession No. AF085716, Adeno-associated virus 5 DNA binding trs helicase (Rep22) and capsid protein (VP1) genes, complete cds, Feb. 9, 1999.
Genbank Accession No. AX753246, Sequence 1 from Patent EP1310571, Jun. 23, 2003.
Genbank Accession No. AX753249, Sequence 4 from Patent EP1310571, Jun. 23, 2003.
Genbank Accession No. NC_001829, Adeno-associated virus—4, complete genome, Aug. 13, 2018.
Genbank Accession No. NC_001862, Adeno-associated virus 6, complete genome, Jan. 12, 2004.
Genbank Accession No. NC_002077, Adeno-associated virus—1, complete genome, Aug. 13, 2018.
Genbank Accession No. J01901, Adeno-associated virus 2, complete genome, Apr. 27, 1993.
GenBank Accession No. U89790.1, Adeno-associated virus 4, complete genome, Aug. 21, 2017.
Govoni et al., Ongoing therapeutic trials and outcome measures for Duchenne muscular dystrophy. Cell Mol. Life Sci., 70(23):4585-602 (2013).
Griffin et al., Defective membrane fusion and repair in Anoctamin5-deficient muscular dystrophy, Hum. Mol. Genet., 25(10):1900-1911 (May 2016).
Hakim et al., The passive mechanical properties of the extensor digitorum longus muscle are compromised in 2- to 20-mo-old mdx mice, J. Appl. Physiol., 110(6):1656-63 (Jun. 2011).
Herzog et al., Stable gene transfer and expression of human blood coagulation factor IX after intramuscular injection of recombinant adeno-associated virus, Proc. Natl. Acad. Sci. USA. 94:5804-9 (1997).
Hicks et al., A founder mutation in Anoctamin 5 is a major cause of limb-girdle muscular dystrophy, Brain, 134(Pt. 1):171-82 (Jan. 2011).
International Application No. PCT/US2016/061703, International Preliminary Report on Patentability, dated May 15, 2018.
International Application No. PCT/US2016/061703, International Search Report and Written Opinion, dated Feb. 2, 2017.
Johnson et al., Muscle creatine kinase sequence elements regulating skeletal and cardiac muscle expression in transgenic mice, Mol. Cell Biol., 9(8):3393-9 (Aug. 1989).
Kajigaya et al., Self-assembled B19 parvovirus capsids, produced in a baculovirus system, are antigenically and immunogenically similar to native virions, Proc. Natl. Acad. Sci. USA, 88(11):4646-50 (Jun. 1991).
Kessler et al., Gene delivery to skeletal muscle results in sustained expression and systemic delivery of a therapeutic protein, Proc. Natl. Acad. Sci. USA. 93:14082-7 (1996).
Kirnbauer et al., Virus-like particles of bovine papillomavirus type 4 in prophylactic and therapeutic immunization, Virology, 219(1):37-44 (May 1996).
Kobayashi et al., Sarcolemma-localized nNOS is required to maintain activity after mild exercise, Nature, 456(7221):511-5 (Nov. 2008).
Lewis et al., Generation of neutralizing activity against human immunodeficiency virus type 1 in serum by antibody gene transfer, J. Virol. 76:8769-75 (2002).
Li et al., Electrical impedance myography for the in vivo and ex vivo assessment of muscular dystrophy (mdx) mouse muscle, Muscle Nerve, 49(6):829-35 (Jun. 2014).
Li et al., Electrophysiologic biomarkers for assessing disease progression and the effect of riluzole in SOD1 G93A ALS mice, PLoS One, 8(6):e65976 (Jun. 2013).
Liu et al., Adeno-associated virus-mediated microdystrophin expression protects young mdx muscle from contraction-induced injury, Mol. Ther., 11(2):245-56 (Feb. 2005).
Mader et al., A steroid-inducible promoter for the controlled overexpression of cloned genes in eukaryotic cells, Proc. Natl. Acad. Sci. USA, 90(12):5603-7 (Jun. 1993).
Monjaret et al., The phenotype of dysferlin-deficient mice is not rescued by adeno-associated virus-mediated transfer of anoctamin 5, Hum. Gene Ther. Clin. Dev., 24(2):65-76 (Jun. 2013).
Moorwood et al., Isometric and eccentric force generation assessment of skeletal muscles isolated from murine models of muscular dystrophies, J. Vis. Exp., (71):e50036 (Jan. 2013).
Mori et al., Two novel adeno-associated viruses from cynomolgus monkey: pseudotyping characterization of capsid protein, Virology. 330:375-83 (2004).
Moroccan Patent Application No. 42736, Search Report with Opinion on Patentability, dated Jun. 14, 2018.
Murphy et al., Long-term correction of obesity and diabetes in genetically obese mice by a single intramuscular injection of recombinant adeno-associated virus encoding mouse leptin, Proc. Natl. Acad. Sci. USA. 94:13921-6 (1997).
Muscat et al., Multiple 5'-flanking regions of the human alpha-skeletal actin gene synergistically modulate muscle-specific expression, Mol. Cell. Biol. 7:4089-99 (1987).
Muzyczka, Use of adeno-associated virus as a general transduction vector for mammalian cells, Curr. Top. Microbiol. Immunol. 158:97-129 (1992).

(56) References Cited

OTHER PUBLICATIONS

Pavlovicova et al., Structure and composition of tubular aggregates of skeletal muscle fibres, Gen. Physiol. Biophys., 22(4):425-40 (Dec. 2003).
Penttila et al., Eight new mutations and the expanding phenotype variability in muscular dystrophy caused by ANO5, Neurology, 78(12):897-903 (Mar. 2012).
Powers et al., Exercise-induced oxidative stress in humans: cause and consequences, Free Radic. Biol. Med., 51(5):942-50 (Sep. 2011).
Rabinowitz et al., Cross-packaging of a single adeno-associated virus (AAV) type 2 vector genome into multiple AAV serotypes enables transduction with broad specificity, J. Virol., 76(2):791-801 (Jan. 2002).
Rafael-Fortney et al., Early treatment with lisinopril and spironolactone preserves cardiac and skeletal muscle in Duchenne muscular dystrophy mice, Circulation, 124(5):582-8 (Aug. 2011).
Rodino-Klapac et al., A translational approach for limb vascular delivery of the micro-dystrophin gene without high volume or high pressure for treatment of Duchenne muscular dystrophy, J. Transl. Med., 5:45 (Sep. 2007).
Ruffing et al., Mutations in the carboxy terminus of adeno-associated virus 2 capsid proteins affect viral infectivity: lack of an RGD integrin-binding motif, J. Gen. Virol. 75:3385-92 (1994).
Rutledge et al., Infectious clones and vectors derived from adeno-associated virus (AAV) serotypes other than AAV type 2, J. Virol., 7291):309-19 (Jan. 1998).
Sambrook et al., Molecular Cloning: A Laboratory Manual, Cold Spring Harbor Laboratory, Cold Spring Harbor, N.Y. (2nd ed. 1989).
Semenza et al., Hypoxia-inducible nuclear factors bind to an enhancer element located 3' to the human erythropoietin gene, Proc. Natl. Acad. Sci. USA, 88(13):5680-4 (Jul. 1991).
Smith et al., Modification and secretion of human interleukin 2 produced in insect cells by a baculovirus expression vector, Proc. Natl. Acad. Sci. USA, 82(24):8404-8 (1985).
Sondergaard et al., AAV.Dysferlin Overlap Vectors Restore Function in Dysferlinopathy Animal Models, Ann. Clin. Transl. Neurol., 293):256-70 (Mar. 2015).
Srivastava et al., Nucleotide sequence and organization of the adeno-associated virus 2 genome, J. Virol. 75:555-64 (1994).
Strobel et al., Antioxidant supplementation reduces skeletal muscle mitochondrial biogenesis, Med. Sci. Sports Exerc., 43(6):1017-24 (Jun. 2011).
Voikar et al., Long-term individual housing in C57BL/6J and DBA/2 mice: assessment of behavioral consequences, Genes Brain Behav., 4(4):240-52 (Jun. 2005).
Wein et al., Translation from a DMD exon 5 IRES results in a functional dystrophin isoform that attenuates dystrophinopathy in humans and mice, Nat. Med., 20(9):992-1000 (Sep. 2014).
Weintraub et al., The myoD gene family: nodal point during specification of the muscle cell lineage, Science. 251:761-6 (1991).
Wu et al., Mutational analysis of the adeno-associated virus type 2 (AAV2) capsid gene and construction of AAV2 vectors with altered tropism, J. Virol., 74(18):8635-47 (Sep. 2000).
Xiao et al., Efficient long-term gene transfer into muscle tissue of immunocompetent mice by adeno-associated virus vector, J. Virol. 70:8098-108 (1996).
Yan et al., Inverted terminal repeat sequences are important for intermolecular recombination and circularization of adeno-associated virus genomes, J. Virol., 79(1):364-79 (Jan. 2005).
Zhao et al., BPV1 E2 protein enhances packaging of full-length plasmid DNA in BPV1 pseudovirions, Virology, 272(2):382-93 (Jul. 2000).
Payne et al., Nutritional therapy improves function and complements corticosteroid intervention in mdx mice, Muscle Nerve, 33(1):66-77 (2006).
NCBI Reference Sequence: "anoctamin-5 isoform a [*Homo sapiens*]", GenPept, Mar. 15, 2015, NP_998764.1.
Witting et al., Anoctamin 5 muscular dystrophy in Denmark: prevalence, genotypes, phenotypes, cardiac findings, and muscle protein expression, Journal of Neurology, 260: 2084-2093 (2013).
Genbank Accession No. BC172489.1, Synthetic construct *Homo sapiens* clone IMAGE:100069183, MGC:199194 anoctamin 5 (ANO5) mRNA, encodes complete protein, Mar. 16, 2009.

\* cited by examiner

METHODS OF TREATING MUSCULAR DYSTROPHY

This application claims priority to U.S. Provisional Patent Application No. 62/254,539, filed on Nov. 12, 2015 and U.S. Provisional Patent Application No. 62/419,793, filed Nov. 9, 2016, which are incorporated by reference herein in their entirety.

FIELD OF INVENTION

The invention provides for AAV vectors expressing the ANO5 gene and antioxidant therapy as methods of inducing muscle regeneration and a method of treating muscular dystrophy.

BACKGROUND

The importance of muscle mass and strength for daily activities such as locomotion and breathing and for whole body metabolism is unequivocal. Deficits in muscle function produce muscular dystrophies (MDs) that are characterized by muscle weakness and wasting and have serious impacts on quality of life. The most well-characterized MDs result from mutations in genes encoding members of the dystrophin-associated protein complex (DAPC). These MDs result from membrane fragility associated with the loss of sarcolemmal-cytoskeleton tethering by the DAPC. In contrast, a subset of other MDs is thought to be caused by defects in sarcolemmal repair. Owing to the mechanical stress the sarcolemma experiences during contraction, even healthy muscle is in constant need of repair mechanisms to patch injured membrane. Sarcolemmal patch repair relies on the fusion of membrane vesicles at sites of damage, and the attenuation of this process is putatively considered a major cause of dysferlinopathies, MDs caused by mutations in dysferlin.

Recently, a new MD with features similar to dysferlinopathies and characterized by sarcolemmal lesions has been linked to recessive mutations in ANO5 (TMEM16E). ANO5 mutations produce limb-girdle muscular dystrophy type 2L (LGMD2L) and Miyoshi myopathy dystrophy type 3 (MMD3). The phenotype associated with ANO5 mutations is variable, but typically the disease presents in adulthood (age 20 to 50) with proximal lower limb weakness, high serum creatine kinase levels, asymmetric muscle atrophy and weakness and is typically accompanied by sarcolemmal lesions, similar to dysferlinopathy (Bolduc et al., *American journal of human genetics* 86, 213-221 (2010)), Hicks et al., *Brain: a journal of neurology* 134, 171-182 (2011), Bouquet et al., *Revue neurologique* 168, 135-141 (2012)). To date, ~72 different ANO5 mutations have been reported in MD patients, and screens for ANO5 mutations in LGMD patients lacking mutations in other known LGMD genes indicate that ANO5 mutations may be one of the more common causes of LGMD (Bolduc et al., *American journal of human genetics* 86, 213-221 (2010)), Hicks et al., *Brain: a journal of neurology* 134, 171-182 (2011), Penttila et al., *Neurology* 78, 897-903 (2012)).

The Anoctamin/TMEM16 family has been functionally split into two categories. The founding members, ANO1 (TMEM16A) and ANO2 (TMEM16B) encode calcium-activated chloride channels, while other ANOs fail to conduct chloride currents and have been identified for their roles in phospholipid scrambling (PLS). However, ANO5 has not been found to exhibit either of these two activities at suggesting a novel function in skeletal muscle. Given this novelty, it remains unclear how the deficiency in ANO5 function elicits a LGMD phenotype, and specifically why Ano5 mutations manifest in a clinically similar way to dysferlin-associated MD.

Adeno-associated virus (AAV) is a replication-deficient parvovirus, the single-stranded DNA genome of which is about 4.7 kb in length including 145 nucleotide inverted terminal repeat (ITRs). There are multiple serotypes of AAV. The nucleotide sequences of the genomes of the AAV serotypes are known. For example, the nucleotide sequence of the AAV serotype 2 (AAV2) genome is presented in Srivastava et al., *J Virol*, 45: 555-564 (1983) as corrected by Ruffing et al., *J Gen Virol*, 75: 3385-3392 (1994). As other examples, the complete genome of AAV-1 is provided in GenBank Accession No. NC_002077; the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively (see also U.S. Pat. Nos. 7,282,199 and 7,790,449 relating to AAV-8); the AAV-9 genome is provided in Gao et al., *J. Virol.*, 78: 6381-6388 (2004); the AAV-10 genome is provided in *Mol. Ther.*, 13(1): 67-76 (2006); and the AAV-11 genome is provided in *Virology*, 330(2): 375-383 (2004). The sequence of the AAV rh.74 genome is provided herein. Cis-acting sequences directing viral DNA replication (rep), encapsidation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (e.g., at AAV2 nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

Multiple studies have demonstrated long-term (>1.5 years) recombinant AAV-mediated protein expression in muscle. See, Clark et al., *Hum Gene Ther,* 8: 659-669 (1997); Kessler et al., *Proc Nat. Acad Sc. USA,* 93: 14082-14087 (1996); and Xiao et al., *J Virol,* 70: 8098-8108 (1996). See also, Chao et al., *Mol Ther,* 2:619-623 (2000) and Chao et al., *Mol Ther,* 4:217-222 (2001). Moreover, because muscle is highly vascularized, recombinant AAV transduction has resulted in the appearance of transgene products in the systemic circulation following intramuscular injection as described in Herzog et al., *Proc Natl Acad Sci USA,* 94: 5804-5809 (1997) and Murphy et al., *Proc Natl Acad Sci USA,* 94: 13921-13926 (1997). Moreover, Lewis et al., *J Virol,* 76: 8769-8775 (2002) demonstrated that skeletal myofibers possess the necessary cellular factors for correct antibody glycosylation, folding, and secretion, indicating that muscle is capable of stable expression of secreted protein therapeutics.

As shown herein, disruption of the Ano5 gene in mice produces several dystrophic muscle histopathogenic features, exercise intolerance, dysfunction in sarcolemmal repair, and myoblast fusion defects. In addition, the data provided demonstrates that these defects are related to changes in subcellular membrane and/or membrane and/or sarcolemmal membrane dynamics mediated by ANO5. The present invention relates to using AAV vectors expressing the Ano5 gene in methods of inducing muscle repair and/or treating MD.

SUMMARY OF INVENTION

The present invention is directed to AAV vectors comprising a nucleotide sequence encoding the ANO5 protein or a functionally active fragment thereof. The experiments described in the Examples 1-4 demonstrate an essential role for Ano5 in muscle regeneration and repair. Loss of ANO5 causes a dystrophic phenotype in mice, reminiscent of LGMD2L patients, with mild histopathology that varies among muscles, exercise intolerance, impaired regeneration, and elevated creatine kinase levels. Mitochondrial abnormalities were observed in both young and aged Ano5$^{-/-}$ mice. In addition to the structural defect of the mitochondria displayed through electron microscopic imaging, citrate synthase quantification assays also demonstrated that the mitochondria have a functional deficit. Quantitative enzyme analysis of citrate synthase suggests the presence of damaged mitochondria. These results suggest that mitochondrial abnormalities may be a secondary effect caused by the loss of the Anoctamin 5 protein. The experiments described herein demonstrate an attenuation of sarcolemmal patch repair in Ano5$^{-/-}$ fibers that is rescued by viral expression of human ANO5 and find that the disruption of Ano5 perturbs the fusogenic quality of primary myoblasts.

In one embodiment, the invention provides for a recombinant AAV vector comprising a polynucleotide comprising an ANO5 nucleic acid sequence. The ANO5 nucleic acid sequence is set out as Genbank Accession No. NM_213599.2 (SEQ ID NO: 13). An exemplary nucleic acid sequence encoding the ANO5 protein in an AAV vector is set out as SEQ ID NO: 1. The recombinant vectors of the present invention comprise a polynucleotide sequence that is at least is at least 85% identical to nucleic acid of SEQ ID NO:1 or SEQ ID NO: 13 or comprise a nucleotide that hybridizes under stringent condition to the nucleotide sequence of SEQ ID NO: 1 or SEQ ID NO: 13 or comprises a fragment of nucleic acid of SEQ ID NO: 1 or SEQ ID NO: 13 encoding a protein that exhibits ANO5 activity. In one aspect, the recombinant AAV vectors of the invention are AAV1, AAV2, AAV4, AAV5, AAV6, AAV7, AAV8, AAV9, AAV10, AAV11, AAV12, AAV13 or AAV rh.74.

The recombinant AAV vectors of the invention comprise a fragment of SEQ ID NO: 1 that encodes a protein that comprise a domain that is involved in PLS activity and said protein retains PLS activity. In another embodiment, the AAV vector comprises a fragment of SEQ ID NO: 1 or SEQ ID NO: 13 that encodes a protein that retains ANO5 activity.

The recombinant AAV vectors of the invention comprise a polynucleotide sequence that is, e.g., at least 65%, at least 70%, at least 75%, at least 80%, 81%, 82%, 83%, 84%, 85%, 86%, 87%, 88%, or 89%, more typically at least 90%, 91%, 92%, 93%, or 94% and even more typically at least 95%, 96%, 97%, 98% or 99% sequence identity to SEQ ID NO: 1 or SEQ ID NO: 13, wherein the polynucleotide encodes a protein that retains ANO5 activity.

The recombinant AAV vectors of the invention comprise a polynucleotide sequence encoding a ANO5 protein that is, e.g., at least at least 65%, at least 70%, at least 75%, at least 80%, 81%, 82%, 83%, 84%, 85%, 86%, 87%, 88%, or 89%, more typically at least 90%, 91%, 92%, 93%, or 94% and even more typically at least 95%, 96%, 97%, 98% or 99% sequence identity to SEQ ID NO: 2, wherein the polynucleotide encodes a protein that retains ANO5 activity The recombinant AAV vectors of the invention comprise a polynucleotide sequence that hybridizes under stringent conditions to the nucleic acid sequence of SEQ ID NOS: 1 or SEQ ID NO: 13, or compliments thereof, which fragment is greater than about 5 nucleotides, preferably 7 nucleotides, more preferably greater than 9 nucleotides and most preferably greater than 17 nucleotides. Fragments of, e.g., 15, 17, or 20 nucleotides or more that are selective for (i.e., specifically hybridize to any one of the polynucleotides of the invention) are contemplated and these fragment retain ANO5 activity. Probes capable of specifically hybridizing to a polynucleotide can differentiate NTHi polynucleotide sequences of the invention from other polynucleotide sequences in the same family of genes or can differentiate NTHi genes from other bacterial genes, and are preferably based on unique nucleotide sequences.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015 M sodium citrate at 65-68° C. or 0.015 M sodium chloride, 0.0015M sodium citrate, and 50% formamide at 42° C. See Sambrook et al., Molecular Cloning: A Laboratory Manual, 2nd Ed., Cold Spring Harbor Laboratory, (Cold Spring Harbor, N.Y. 1989). More stringent conditions (such as higher temperature, lower ionic strength, higher formamide, or other denaturing agent) may also be used, however, the rate of hybridization will be affected. In instances wherein hybridization of deoxyoligonucleotides is concerned, additional exemplary stringent hybridization conditions include washing in 6×SSC 0.05% sodium pyrophosphate at 37° C.

(for 14-base oligos), 48° C. (for 17-base oligos), 55° C. (for 20-base oligos), and 60° C. (for 23-base oligos).

Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, NaDodSO4, (SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, however, at typical ionic strength conditions, the rate of hybridization is nearly independent of pH. See Anderson et al., Nucleic Acid Hybridisation: A Practical Approach, Ch. 4, IRL Press Limited (Oxford, England). Hybridization conditions can be adjusted by one skilled in the art in order to accommodate these variables and allow DNAs of different sequence relatedness to form hybrids.

In another aspect, the recombinant AAV vectors of the invention may be operably linked to a muscle-specific control element. For example the muscle-specific control element is human skeletal actin gene element, cardiac actin gene element, myocyte-specific enhancer binding factor MEF, murine creatine kinase enhancer element (MCK), triple copies of the MCK (tMCK), skeletal fast-twitch troponin C gene element, slow-twitch cardiac troponin C gene element, the slow-twitch troponin I gene element, hypoxia-inducible nuclear factors, steroid-inducible element or glucocorticoid response element (GRE).

In another embodiment, the invention provides for methods of producing a recombinant AAV vector particle comprising culturing a cell that has been transfected with any recombinant AAV vector of the invention and recovering recombinant AAV particles from the supernatant of the transfected cells. The invention also provides for viral particles comprising any of the recombinant AAV vectors of the invention.

In another embodiment, the invention provides for methods of treating muscular dystrophy comprising administering a therapeutically effective amount of any recombinant AAV vector of the invention to a subject in need thereof. In one aspect, the subject in need has a recessive mutation in the ANO5 gene. The methods may treat dysferlin-associated muscular dystrophy, limb girdle muscular dystrophy type 2L, Miyoshi myopathy type 3, Bethlem myopathy, calpainopathy, desmin myopathy, dysferlinopathy, myofibrillar myopathy, sarcoglycanopathie or ZASP-related myopathy. In addition, any of the foregoing methods to treat muscular dystrophy further comprise the step of administrating a therapeutically effective amount of an antioxidant composition to a subject in need thereof. For example, the antioxidant composition comprises at least one of a coenzyme Q10, lipoic acid, vitamin, carotenoid, vitamin cofactor, mineral, polyphenol, or flavonoid. In particular, the antioxidant composition comprises coenzyme Q10, lipoic acid and vitamin E.

In a further embodiment, the invention provides for methods of regenerating muscle in a subject in need comprising administering a therapeutically effective amount of any recombinant AAV vector of the invention to subject in need thereof. In one aspect, the subject in need has a recessive mutation in the ANO5 gene. In another aspect, the subject in need is suffering from muscular dystrophy such as dysferlin-associated muscular dystrophy, limb girdle muscular dystrophy type 2L, Miyoshi myopathy type 3, Bethlem myopathy, calpainopathy, desmin myopathy, dysferlinopathy, myofibrillar myopathy, sarcoglycanopathie or ZASP-related myopathy. In addition, any of the foregoing methods to regenerate muscle further comprise the step of administrating a therapeutically effective amount of an antioxidant composition to a subject in need thereof. For example, the antioxidant composition comprises at least one of a coenzyme Q10, lipoic acid, vitamin, carotenoid, vitamin cofactor, mineral, polyphenol, or flavonoid. In particular, the antioxidant composition comprises coenzyme Q10, lipoic acid and vitamin E.

In another embodiment, the invention provides for methods of treating chronic muscle wasting comprising administering a therapeutically effective amount of any of the recombinant AAV vectors of the invention to subject in need thereof. In one aspect, the subject in need has a recessive mutation in the ANO5 gene. In another aspect, the subject in need is suffering from muscular dystrophy such as dysferlin-associated muscular dystrophy, limb girdle muscular dystrophy type 2L or Miyoshi myopathy type 3, Bethlem myopathy, calpainopathy, desmin myopathy, dysferlinopathy, myofibrillar myopathy, sarcoglycanopathie or ZASP-related myopathy. In addition, any of the foregoing methods to treat chronic muscle wasting further comprise the step of administrating a therapeutically effective amount of an antioxidant composition to a subject in need thereof. For example, the antioxidant composition comprises at least one of a coenzyme Q10, lipoic acid, vitamin, carotenoid, vitamin cofactor, mineral, polyphenol, or flavonoid. In particular, the antioxidant composition comprises coenzyme Q10, lipoic acid and vitamin E.

The invention also provides for a composition comprising any recombinant AAV vector of the invention for the treatment of muscular dystrophy or chronic muscle wasting syndrome in a subject in need. The invention also provides for composition comprising any recombinant AAV vector of the invention for the regeneration of muscle in a subject in need. In one aspect, the composition of the invention is administered to a subject having recessive mutation in the ANO5 gene. In another aspect, the composition of the invention is administered to a subject in suffering from muscular dystrophy such as dysferlin-associated muscular dystrophy, limb girdle muscular dystrophy type 2L, Miyoshi myopathy type 3, Bethlem myopathy, calpainopathy, desmin myopathy, dysferlinopathy, myofibrillar myopathy, sarcoglycanopathie or ZASP-related myopathy. Any of the compositions of the invention are formulated for intramuscular or intravenous injection. Any of the compositions of the invention further comprise a therapeutically effective amount of an antioxidant composition. For example, the antioxidant composition comprises at least one of a coenzyme Q10, lipoic acid, vitamin, carotenoid, vitamin cofactor, mineral, polyphenol, or flavonoid. In particular, the antioxidant composition comprises coenzyme Q10, lipoic acid and vitamin E.

In another embodiment, the invention provides for use of any recombinant AAV vector of the invention for the preparation of a medicament for treatment of muscular dystrophy or chronic muscle wasting syndrome in a subject in need thereof. In addition, the invention provides for use of any of the recombinant AAV vectors of the invention for the preparation of a medicament for regenerating muscle in subject need thereof. In one aspect, the medicament is administered to a subject having recessive mutation in the ANO5 gene. In another aspect, the medicament of the invention is administered to a subject in suffering from muscular dystrophy such as dysferlin-associated muscular dystrophy, limb girdle muscular dystrophy type 2L, Miyoshi myopathy type 3, Bethlem myopathy, calpainopathy, desmin myopathy, dysferlinopathy, myofibrillar myopathy, sarcoglycanopathie or ZASP-related myopathy. Any of the medicaments of the invention are formulated for intramuscular or intravenous injection. Any of the medicaments of the invention further comprise a therapeutically effective amount of an antioxidant composition. For example, the antioxidant composition comprises at least one of a coenzyme Q10, lipoic acid, vitamin, carotenoid, vitamin cofactor, mineral, polyphenol, or flavonoid. In particular, the antioxidant composition comprises coenzyme Q10, lipoic acid and vitamin E.

In another embodiment, the invention provides for methods of treating muscular dystrophy or chronic muscle wasting comprising administering a therapeutically effective amount of antioxidant composition to a subject in need thereof. The antioxidant composition comprises at least one of a coenzyme Q10, lipoic acid, vitamin, carotenoid, vitamin cofactor, mineral, polyphenol, or flavonoid. In some aspects, the antioxidant composition comprises coenzyme Q10, lipoic acid and vitamin E. In one aspect, the subject in need has a recessive mutation in the ANO5 gene. In another aspect, oxidative stress is reduced in skeletal muscle of the subject. In another aspect, the skeletal muscle function of the subject is improved. The In another aspect, the subject is suffering from dysferlin-associated muscular dystrophy, limb girdle muscular dystrophy type 2L, Miyoshi myopathy type 3, Bethlem myopathy, calpainopathy, desmin myopathy, dysferlinopathy, myofibrillar myopathy, sarcoglycanopathie or ZASP-related myopathy.

The invention also provides for methods for slowing the progression of muscular dystrophy or chronic muscle wasting comprising administering a therapeutically effective amount of an antioxidant composition to a subject in need thereof. The antioxidant composition comprises at least one of a coenzyme Q10, lipoic acid, vitamin, carotenoid, vitamin cofactor, mineral, polyphenol, or flavonoid. In some aspects, the antioxidant composition comprises coenzyme Q10, lipoic acid and vitamin E. In one aspect, the subject in need has a recessive mutation in the ANO5 gene. In another aspect, oxidative stress is reduced in skeletal muscle of the subject. In another aspect, the skeletal muscle function of the subject is improved. In another aspect, the subject is suffering from dysferlin-associated muscular dystrophy, limb girdle muscular dystrophy type 2L, Miyoshi myopathy type 3, Bethlem myopathy, calpainopathy, desmin myopathy, dysferlinopathy, myofibrillar myopathy, sarcoglycanopathie or ZASP-related myopathy.

In any of the methods of the invention, the antioxidant composition is administered orally. In any of the methods of the invention, the antioxidants are administered in the same composition or the antioxidants are administered in separate compositions. If the antioxidants are administered separately but concurrently. In addition, in any of the methods of the invention, the antioxidants are administered at separate times or consecutively. In any of the methods of the invention, the antioxidant composition is administered once daily, once weekly, twice weekly, once every two weeks, once every three weeks, monthly or once every two months.

The invention also provides for a composition comprising a therapeutically effective amount of an antioxidant composition. The antioxidant composition comprises at least one of a coenzyme Q10, lipoic acid, vitamin, carotenoid, vitamin cofactor, mineral, polyphenol, or flavonoid for the treatment of muscular dystrophy or chronic muscle wasting syndrome in a subject in need.

The invention also provides for composition comprising a therapeutically effective amount of an antioxidant composition. The antioxidant compositions comprises at least one of a coenzyme Q10, lipoic acid, vitamin, carotenoid, vitamin cofactor, mineral, polyphenol, or flavonoid for slowing the progression of muscular dystrophy or chronic muscle wasting in a subject in need. In some aspects, the antioxidant composition comprises coenzyme Q10, lipoic acid and vitamin E.

In one aspect, any of the compositions of the invention is administered to a subject having recessive mutation in the ANO5 gene. In another aspect, oxidative stress is reduced in skeletal muscle of the subject after administration of the composition. In another aspect, the skeletal muscle function of the subject is improved after administration of the composition. In another aspect, any of the compositions of the invention is administered to a subject suffering from muscular dystrophy such as dysferlin-associated muscular dystrophy, limb girdle muscular dystrophy type 2L, Miyoshi myopathy type 3, Bethlem myopathy, calpainopathy, desmin myopathy, dysferlinopathy, myofibrillar myopathy, sarcoglycanopathie or ZASP-related myopathy. Any of the compositions of the invention are formulated for intramuscular or intravenous injection.

In another embodiment, the invention provides for use of an antioxidant composition for the preparation of a medicament for the treatment of muscular dystrophy or chronic muscle wasting syndrome in a subject in need thereof. The antioxidant composition in any of the medicaments of the invention comprises at least one of a coenzyme Q10, lipoic acid, vitamin, carotenoid, vitamin cofactor, mineral, polyphenol, or flavonoid.

In addition, the invention provides for use of an antioxidant composition for the preparation of a medicament for regenerating muscle in a subject in need thereof. The antioxidant composition in any of the medicaments of the invention comprises at least one of a coenzyme Q10, lipoic acid, vitamin, carotenoid, vitamin cofactor, mineral, polyphenol, or flavonoid. In some aspects, the antioxidant composition comprises coenzyme Q10, lipoic acid and vitamin E.

In addition, the invention provides for use of an antioxidant composition for the preparation of a medicament for slowing the progression of muscular dystrophy or muscle wasting syndrome in a subject in need thereof. The antioxidant composition in any of the medicaments of the invention comprises at least one of a coenzyme Q10, lipoic acid, vitamin, carotenoid, vitamin cofactor, mineral, polyphenol, or flavonoid. In some aspects, the antioxidant composition comprises coenzyme Q10, lipoic acid and vitamin E.

Any of the medicaments of the invention are administered to a subject having recessive mutation in the ANO5 gene. In another aspect, oxidative stress is reduced in skeletal muscle of the subject. In another aspect, the skeletal muscle function of the subject is improved. In another aspect, any of the medicaments of the invention is administered to a subject in suffering from muscular dystrophy such as dysferlin-associated muscular dystrophy, limb girdle muscular dystrophy type 2L, Miyoshi myopathy type 3, Bethlem myopathy, calpainopathy, desmin myopathy, dysferlinopathy, myofibrillar myopathy, sarcoglycanopathie or ZASP-related myopathy. In addition, any of the medicaments of the invention are formulated for intramuscular or intravenous injection.

In some embodiments, the antioxidant composition is administered orally. In some aspects, the antioxidants are in the same composition. In other aspects, the antioxidants are in separate compositions. In some aspects, the antioxidants of the antioxidant composition are administered concurrently. In some aspects, the antioxidants of the antioxidant composition are administered at separate times or consecutively. In some embodiments, the antioxidant composition is administered once daily, once weekly, twice weekly, once every two weeks, once every three weeks, monthly or once every two months.

DETAILED DESCRIPTION

Figure 1:
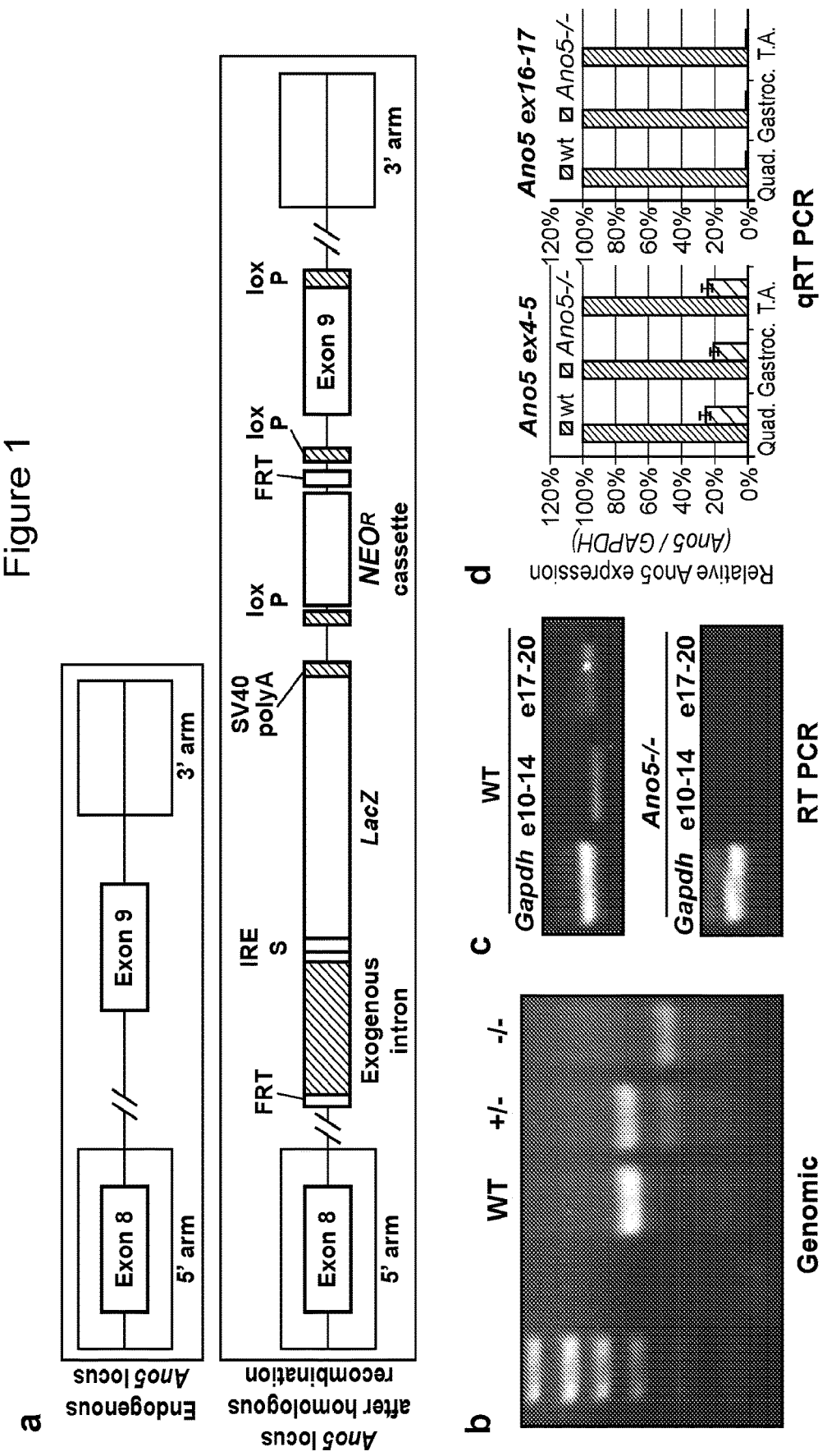
FIG. 1A-1D illustrates generation of the Ano5$^{-/-}$ mouse model. Panel (a) shows an Ano5 targeting vector comprising an exogenous intron and lacZ-encoding exon with a polyadenylation termination signal. The resulting mRNA terminates with exon 8. Panel (b) show genomic DNA isolated from tail clippings of littermates. Lane 1—wild type (WT) mouse, Lanes 2 Ano5$^{+/-}$ mouse, Lane 3 Ano5$^{-/-}$ mouse, WTallele-300 bp fragment, Ano5 allele—200 bp fragment. Panel (c) displays products from RT-PCR displaying no evidence of the Ano5 transcript in Ano5$^{-/-}$ muscle tissue using two primer sets targeting Ano5. Lane 1: GAPDH control; lane 2 e10-14 primers spanning exons 10-14; lane 3 e17-20 primers spanning exons 17-20. Panel (d) demonstrates >99% relative expression reduction of ANO5 at the RNA level was confirmed through qRT-PCR in quadriceps (QD), gastrocnemius (GAS) and tibialis anterior (TA) muscle extracted from the Ano5$^{-/-}$ mouse (P<0.001).

ANO5 plays an essential role in muscle repair and the invention provides for AAV vectors comprising the ANO5 gene for treatment of MD. Disruption of ANO5 closely phenocopies the loss of dysferlin expression in murine models, and dysferlin mutations cause MDs similar to ANO5 myopathies (limb girdle muscular dystrophy 2B (LGMD2B) and Miyoshi myophathy dystrophy 1 (MMD1) vs limb girdle muscular dystrophy 2L (LGMD2L) and Miyoshi myopathy dystrophy 3 (MMD3)).

The Ano5$^{-/-}$ mouse represents an important model for the study of ANO5-myopathy, sarcolemmal repair, and myogenic cell fusion. The experimental evidence provided in the Examples below support methods for gene replacement therapy as a treatment strategy for ANO5-myopathy by partially rescuing the membrane repair phenotype via AAV.ANO5-FLAG treatment of Ano5$^{-/-}$ mice.

AAV

As used herein, the term "AAV" is a standard abbreviation for adeno-associated virus. Adeno-associated virus is a single-stranded DNA parvovirus that grows only in cells in which certain functions are provided by a co-infecting helper virus. There are currently thirteen serotypes of AAV that have been characterized, as shown below in Table 1. General information and reviews of AAV can be found in, for example, Carter, 1989, Handbook of Parvoviruses, Vol. 1, pp. 169-228, and Berns, 1990, Virology, pp. 1743-1764, Raven Press, (New York). However, it is fully expected that these same principles will be applicable to additional AAV serotypes since it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3:1-61 (1974)). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

An "AAV vector" as used herein refers to a vector comprising one or more polynucleotides of interest (or transgenes) that are flanked by AAV terminal repeat sequences (ITRs). Such AAV vectors can be replicated and packaged into infectious viral particles when present in a host cell that has been transfected with a vector encoding and expressing rep and cap gene products.

An "AAV virion" or "AAV viral particle" or "AAV vector particle" refers to a viral particle composed of at least one AAV capsid protein and an encapsidated polynucleotide AAV vector. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector". Thus, production of AAV vector particle necessarily includes production of AAV vector, as such a vector is contained within an AAV vector particle.

An AAV vector may be either single-stranded or double-stranded nucleic acid, having an AAV 5' inverted terminal repeat (ITR) sequence and an AAV 3' ITR flanking a protein-coding sequence operably linked to transcription regulatory elements, i.e., one or more promoters and/or enhancers, and a polyadenylation sequence, and, optionally, one or more introns inserted between exons of the protein-coding sequence. A single-stranded AAV vector refers to nucleic acids that are present in the genome of an AAV virus particle, and can be either the sense strand or the anti-sense strand of the nucleic acid sequences disclosed herein. The size of such single-stranded nucleic acids is provided in bases. A double-stranded AAV vector refers to nucleic acids that are present in the DNA of plasmids, e.g., pUC 19, or genome of a double-stranded virus, e.g., baculovirus, used to express or transfer the AAV vector nucleic acids. The size of such double-stranded nucleic acids in provided in base pairs (bp).

The term "inverted terminal repeat (ITR)" as used herein refers to the art-recognized regions found at the 5' and 3' termini of the AAV genome which function in cis as origins of DNA replication and as packaging signals for the viral genome. AAV ITRs, together with the AAV rep coding region, provide for efficient excision and rescue from, and integration of a nucleotide sequence interposed between two flanking ITRs into a host cell genome. Sequences of certain AAV-associated ITRs are disclosed by Yan et al., J. Virol. 79(1):364-379 (2005) which is herein incorporated by reference in its entirety.

A "transcription control element" refers to nucleotide sequences of a gene involved in regulation of genetic transcription including a promoter, plus response elements, activator and enhancer sequences for binding of transcription factors to aid RNA polymerase binding and promote expression, and operator or silencer sequences to which repressor proteins bind to block RNA polymerase attachment and prevent expression.

AAV "rep" and "cap" genes are genes encoding replication and encapsidation proteins, respectively. AAV rep and cap genes have been found in all AAV serotypes examined to date, and are described herein and in the references cited. In wild-type AAV, the rep and cap genes are generally found adjacent to each other in the viral genome (i.e., they are "coupled" together as adjoining or overlapping transcriptional units), and they are generally conserved among AAV serotypes. AAV rep and cap genes are also individually and collectively referred to as "AAV packaging genes." The AAV cap gene in accordance with the present invention encodes a Cap protein which is capable of packaging AAV vectors in the presence of rep and adeno helper function and is capable of binding target cellular receptors. In some embodiments, the AAV cap gene encodes a capsid protein having an amino acid sequence derived from a particular AAV serotype, for example the serotypes shown in Table 1 and AAV rh.74 (see U.S. Pat. No. 9,434,928). Other types of rAAV variants, for example rAAV with capsid mutations, are also contemplated. See, for example, Marsic et al., Mol Ther, 22(11): 1900-1909 (2014).

TABLE 1

| AAV serotypes | |
|---|---|
| AAV Serotype | Genbank Accession No. |
| AAV-1 | NC_002077.1 |
| AAV-2 | NC_001401.2 |
| AAV-3 | NC_001729.1 |
| AAV-3B | AF028705.1 |
| AAV-4 | NC_001829.1 |
| AAV-5 | NC_006152.1 |
| AAV-6 | AF028704.1 |
| AAV-7 | NC_006260.1 |
| AAV-8 | NC_006261.1 |
| AAV-9 | AX753250.1 |

TABLE 1-continued

AAV serotypes

| AAV Serotype | Genbank Accession No. |
| --- | --- |
| AAV-10 | AY631965.1 |
| AAV-11 | AY631966.1 |
| AAV-12 | DQ813647.1 |
| AAV-13 | EU285562.1 |

The AAV sequences employed for the production of AAV can be derived from the genome of any AAV serotype. Generally, the AAV serotypes have genomic sequences of significant homology at the amino acid and the nucleic acid levels, provide a similar set of genetic functions, produce virions which are essentially physically and functionally equivalent, and replicate and assemble by practically identical mechanisms. For the genomic sequence of AAV serotypes and a discussion of the genomic similarities see, for example, GenBank Accession number U89790; GenBank Accession number J01901; GenBank Accession number AF043303; GenBank Accession number AF085716; Chlorini et al., J. Vir. 71: 6823-33(1997); Srivastava et al., J. Vir. 45:555-64 (1983); Chlorini et al., J. Vir. 73:1309-1319 (1999); Rutledge et al., J. Vir. 72:309-319 (1998); and Wu et al., J. Vir. 74: 8635-47 (2000).

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. The Rep genes encode the Rep proteins, Rep78, Rep68, Rep52, and Rep40. Rep78 and Rep68 are transcribed from the p5 promoter, and Rep 52 and Rep40 are transcribed from the p19 promoter. The cap genes encode the VP proteins, VP1, VP2, and VP3. The cap genes are transcribed from the p40 promoter.

In some embodiments, a nucleic acid sequence encoding an AAV capsid protein is operably linked to expression control sequences for expression in a specific cell type, such as Sf9 or HEK cells. Techniques known to one skilled in the art for expressing foreign genes in insect host cells or mammalian host cells can be used to practice the invention. Methodology for molecular engineering and expression of polypeptides in insect cells is described, for example, in Summers and Smith. 1986. A Manual of Methods for Baculovirus Vectors and Insect Culture Procedures, Texas Agricultural Experimental Station Bull. No. 7555, College Station, Tex.; Luckow. 1991. In Prokop et al., Cloning and Expression of Heterologous Genes in Insect Cells with Baculovirus Vectors' Recombinant DNA Technology and Applications, 97-152; King, L. A. and R. D. Possee, 1992, The baculovirus expression system, Chapman and Hall, United Kingdom; O'Reilly, D. R., L. K. Miller, V. A. Luckow, 1992, Baculovirus Expression Vectors: A Laboratory Manual, New York; W.H. Freeman and Richardson, C. D., 1995, Baculovirus Expression Protocols, Methods in Molecular Biology, volume 39; U.S. Pat. No. 4,745,051; US2003148506; and WO 03/074714. A particularly suitable promoter for transcription of a nucleotide sequence encoding an AAV capsid protein is e.g. the polyhedron promoter. However, other promoters that are active in insect cells are known in the art, e.g. the p10, p35 or IE-1 promoters and further promoters described in the above references are also contemplated.

Use of insect cells for expression of heterologous proteins is well documented, as are methods of introducing nucleic acids, such as vectors, e.g., insect-cell compatible vectors, into such cells and methods of maintaining such cells in culture. See, for example, METHODS IN MOLECULAR BIOLOGY, ed. Richard, Humana Press, N J (1995); O'Reilly et al., BACULOVIRUS EXPRESSION VECTORS, A LABORATORY MANUAL, Oxford Univ. Press (1994); Samulski et al., J. Vir. 63:3822-8 (1989); Kajigaya et al., Proc. Nat'l. Acad. Sci. USA 88: 4646-50 (1991); Ruffing et al., J. Vir. 66:6922-30 (1992); Kirnbauer et al., Vir. 219:37-44 (1996); Zhao et al., Vir. 272:382-93 (2000); and Samulski et al., U.S. Pat. No. 6,204,059. In some embodiments, the nucleic acid construct encoding AAV in insect cells is an insect cell-compatible vector. An "insect cell-compatible vector" or "vector" as used herein refers to a nucleic acid molecule capable of productive transformation or transfection of an insect or insect cell. Exemplary biological vectors include plasmids, linear nucleic acid molecules, and recombinant viruses. Any vector can be employed as long as it is insect cell-compatible. The vector may integrate into the insect cells genome but the presence of the vector in the insect cell need not be permanent and transient episomal vectors are also included. The vectors can be introduced by any means known, for example by chemical treatment of the cells, electroporation, or infection. In some embodiments, the vector is a baculovirus, a viral vector, or a plasmid. In a more preferred embodiment, the vector is a baculovirus, i.e. the construct is a baculoviral vector. Baculoviral vectors and methods for their use are described in the above cited references on molecular engineering of insect cells.

Baculoviruses are enveloped DNA viruses of arthropods, two members of which are well known expression vectors for producing recombinant proteins in cell cultures. Baculoviruses have circular double-stranded genomes (80-200 kbp) which can be engineered to allow the delivery of large genomic content to specific cells. The viruses used as a vector are generally *Autographa californica* multicapsid nucleopolyhedrovirus (AcMNPV) or *Bombyx mori* (Bm) NPV) (Kato et al., 2010).

Baculoviruses are commonly used for the infection of insect cells for the expression of recombinant proteins. In particular, expression of heterologous genes in insects can be accomplished as described in for instance U.S. Pat. No. 4,745,051; Friesen et al (1986); EP 127,839; EP 155,476; Vlak et al (1988); Miller et al (1988); Carbonell et al (1988); Maeda et al (1985); Lebacq-Verheyden et al (1988); Smith et al (1985); Miyajima et al (1987); and Martin et al (1988). Numerous baculovirus strains and variants and corresponding permissive insect host cells that can be used for protein production are described in Luckow et al (1988), Miller et al (1986); Maeda et al (1985) and McKenna (1989).

In one aspect, the invention provides rAAV genomes. The rAAV genomes comprise one or more AAV ITRs flanking a polynucleotide sequence encoding the ANO5 protein. If the polynucleotide encodes ANO5 protein, the polynucleotide is operatively linked to transcriptional control DNA, specifically promoter DNA and polyadenylation signal sequence DNA that are functional in target cells, e.g. muscle cells, to form a gene cassette. The gene cassette may also include intron sequences to facilitate processing of the RNA transcript when expressed in mammalian cells. For example, the AAV genome comprises one or more AAV ITRs flanking on ore more exons of the ANO5 gene, such as exon 8 and exon 9 of the ANO5 gene. The AAV genome may also comprise one or more of the following: an intron, a report gene such as Lac-Z 3-galactosidase or neomycin resistance gene, CRE-Lox recombination sites such as Lox P, and an internal ribosome entry site (IRE S).

Methods for Producing Recombinant AAVs

The present disclosure provides materials and methods for producing recombinant AAVs in insect or mammalian cells. In some embodiments, the viral construct further comprises a promoter and a restriction site downstream of the promoter to allow insertion of a polynucleotide encoding one or more proteins of interest, wherein the promoter and the restriction site are located downstream of the 5' AAV ITR and upstream of the 3' AAV ITR. In some embodiments, the viral construct further comprises a posttranscriptional regulatory element downstream of the restriction site and upstream of the 3' AAV ITR. In some embodiments, the viral construct further comprises a polynucleotide inserted at the restriction site and operably linked with the promoter, where the polynucleotide comprises the coding region of a protein of interest. As a skilled artisan will appreciate, any one of the AAV vector disclosed in the present application can be used in the method as the viral construct to produce the recombinant AAV. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions.

In some embodiments, the helper functions are provided by one or more helper plasmids or helper viruses comprising adenoviral or baculoviral helper genes. Non-limiting examples of the adenoviral or baculoviral helper genes include, but are not limited to, E1A, E1B, E2A, E4 and VA, which can provide helper functions to AAV packaging.

Helper viruses of AAV are known in the art and include, for example, viruses from the family Adenoviridae and the family Herpesviridae. Examples of helper viruses of AAV include, but are not limited to, SAdV-13 helper virus and SAdV-13-like helper virus described in US Publication No. 20110201088 (the disclosure of which is incorporated herein by reference), helper vectors pHELP (Applied Viromics). A skilled artisan will appreciate that any helper virus or helper plasmid of AAV that can provide adequate helper function to AAV can be used herein.

In some embodiments, the AAV cap genes are present in a plasmid. The plasmid can further comprise an AAV rep gene. The cap genes and/or rep gene from any AAV serotype (including, but not limited to, AAV1, AAV2, AAV4, AAV5, AAV6, AAV7, AAV8, AAV9, AAV10, AAV11, AAV12, AAV13, AAV rh.74 and any variants thereof) can be used herein to produce the recombinant AAV. In some embodiments, the AAV cap genes encode a capsid from serotype 1, serotype 2, serotype 4, serotype 5, serotype 6, serotype 7, serotype 8, serotype 9, serotype 10, serotype 11, serotype 12, serotype 13 or a variant thereof.

In some embodiments, the insect or mammalian cell can be transfected with the helper plasmid or helper virus, the viral construct and the plasmid encoding the AAV cap genes; and the recombinant AAV virus can be collected at various time points after co-transfection. For example, the recombinant AAV virus can be collected at about 12 hours, about 24 hours, about 36 hours, about 48 hours, about 72 hours, about 96 hours, about 120 hours, or a time between any of these two time points after the co-transfection.

Recombinant AAV can also be produced using any conventional methods known in the art suitable for producing infectious recombinant AAV. In some instances, a recombinant AAV can be produced by using an insect or mammalian cell that stably expresses some of the necessary components for AAV particle production. For example, a plasmid (or multiple plasmids) comprising AAV rep and cap genes, and a selectable marker, such as a neomycin resistance gene, can be integrated into the genome of the cell. The insect or mammalian cell can then be co-infected with a helper virus (e.g., adenovirus or baculovirus providing the helper functions) and the viral vector comprising the 5' and 3' AAV ITR (and the nucleotide sequence encoding the heterologous protein, if desired). The advantages of this method are that the cells are selectable and are suitable for large-scale production of the recombinant AAV. As another non-limiting example, adenovirus or baculovirus rather than plasmids can be used to introduce rep and cap genes into packaging cells. As yet another non-limiting example, both the viral vector containing the 5' and 3' AAV LTRs and the rep-cap genes can be stably integrated into the DNA of producer cells, and the helper functions can be provided by a wild-type adenovirus to produce the recombinant AAV.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595. The foregoing documents are hereby incorporated by reference in their entirety herein, with particular emphasis on those sections of the documents relating to rAAV production.

The invention thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

The rAAV may be purified by methods standard in the art such as by column chromatography or cesium chloride gradients. Methods for purifying rAAV vectors from helper virus are known in the art and include methods disclosed in, for example, Clark et al., *Hum. Gene Ther.*, 10(6): 1031-1039 (1999); Schenpp and Clark, *Methods Mol. Med.*, 69 427-443 (2002); U.S. Pat. No. 6,566,118 and WO 98/09657.

Cell Types Used in AAV Production

The viral particles comprising the AAV vectors of the invention may be introduced using any invertebrate cell type which allows for production of AAV or biologic products and which can be maintained in culture. For example, the insect cell line used can be from *Spodoptera frugiperda*, such as SF9, SF21, SF900+, *drosophila* cell lines, mosquito cell lines, e.g., *Aedes albopictus* derived cell lines, domestic silkworm cell lines, e.g. Bombyxmori cell lines, *Trichoplusia, ni* cell lines such as High Five cells or Lepidoptera cell lines such as *Ascalapha odorata* cell lines. Preferred insect cells are cells from the insect species which are susceptible to baculovirus infection, including High Five, Sf9, Se301, SeIZD2109, SeUCR1, Sf9, Sf900+, Sf21, BTI-TN-5B1-4, MG-1, Tn368, HzAm1, BM-N, Ha2302, Hz2E5 and Ao38.

Baculoviruses are enveloped DNA viruses of arthropods, two members of which are well known expression vectors for producing recombinant proteins in cell cultures. Baculoviruses have circular double-stranded genomes (80-200 kbp) which can be engineered to allow the delivery of large genomic content to specific cells. The viruses used as a vector are generally *Autographa californica* multicapsid nucleopolyhedrovirus (AcMNPV) or *Bombyx mori* (BmNPV) (Kato et al., 2010).

Baculoviruses are commonly used for the infection of insect cells for the expression of recombinant proteins. In particular, expression of heterologous genes in insects can be accomplished as described in for instance U.S. Pat. No. 4,745,051; Friesen et al (1986); EP 127,839; EP 155,476; Vlak et al (1988); Miller et al (1988); Carbonell et al (1988); Maeda et al (1985); Lebacq-Verheyden et al (1988); Smith et al (1985); Miyajima et al (1987); and Martin et al (1988). Numerous baculovirus strains and variants and corresponding permissive insect host cells that can be used for protein production are described in Luckow et al (1988), Miller et al (1986); Maeda et al (1985) and McKenna (1989).

In another aspect of the invention, the methods of the invention are also carried out with any mammalian cell type which allows for replication of AAV or production of biologic products, and which can be maintained in culture. Preferred mammalian cells used can be HEK293, HeLa, CHO, NS0, SP2/0, PER.C6, Vero, RD, BHK, HT 1080, A549, Cos-7, ARPE-19 and MRC-5 cells.

Compositions

In another embodiment, the invention contemplates compositions comprising rAAV and/or antioxidants of the present invention. These compositions may be used to regenerate, enhance or repair muscle and/or improve muscle function.

Compositions of the invention comprise rAAV in a pharmaceutically acceptable carrier. The compositions may also comprise other ingredients such as diluents and adjuvants. Acceptable carriers, diluents and adjuvants are nontoxic to recipients and are preferably inert at the dosages and concentrations employed, and include buffers such as phosphate, citrate, or other organic acids; antioxidants; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

Methods of transducing a target cell with rAAV, in vivo or in vitro, are contemplated by the invention. The in vivo methods comprise the step of administering an effective dose, or effective multiple doses, of a composition comprising a rAAV of the invention to an animal (including a human patient) in need thereof. An effective dose, or effective multiple doses, of a combination of compositions comprising a rAAV of the disclosure to a subject) is a dose that prevents, slows progression of, or ameliorates (eliminates or reduces) muscle pathology associated with the disease being treated. An effect on muscle pathology can be demonstrated by an improvement in one or more measures standard in the art such as: absolute muscle specific force; force decrement during eccentric muscle contractions; serum CK level; serum cardiac troponin level; serum MMP9 level; grip strength; limb torque; limb mobility or flexibility; ambulation; 6 minute walk test; knee flexor or extensor strength; maximal voluntary isometric muscle contraction; North Star Ambulatory Assessment; muscle mass, fat reduction, or edema by limb T2-weighted MRI measures; muscle contractures; limb joint angle; heart function (heart rate, cardiac output, percent fractional shortening, stroke volume); respiration (including respiratory rate, blood oxygenation, need for supplemental oxygen); muscle necrosis; muscle regeneration; muscle wasting; muscle inflammation; muscle calcification; muscle central nucleation; muscle size or myofiber size; lifespan; and dystrophin or laminin alpha 2 surrogate protein expression (utrophin, plectin 1, laminin alpha 5, agrin). See, for example, Forbes et al., *Radiology*, 269(1): 198-207 (2013); Govoni et al., *Cell Mol. Life Sci.*, 70(23): 4585-4602 (2013); and Chandrasekharan and Martin, *Methods Enzymol.*, 479: 291-322 (2010). If a dose is administered prior to development of a disease, the administration is prophylactic. If a dose is administered after the development of a disease, the administration is therapeutic. The treatment of the subject by methods described herein is therefore contemplated to prevent, slow or prevent progression of, diminish the extent of, result in remission (partial or total) of, and/or prolong survival of the disease being treated.

Combination therapies are also contemplated by the invention. Combination as used herein includes both simultaneous treatment or sequential treatments. Combinations of methods of the invention with standard medical treatments (e.g., corticosteroids for muscular dystrophies) are specifically contemplated, as are combinations with novel therapies. In this respect, it may be conceivable induce expression of ANO5 to reduce or inhibit muscle injury, to enhance muscle, or induce muscle repair, and then provide the secondary treatment. Such secondary treatments for Muscular Dystrophy may include the use of antioxidants (e.g. lipoic acid, coenzyme Q10 and α-tocopherol), IGF-1, interfering RNA approaches, exon-skipping, calpain inhibition, dystrophin upregulation, and dystroglycan expression. Further, there may be additions to expression of ANO5 to enhance the muscle boosting effects. For example, addition of IGF-1 or other trophic factors or muscle precursor injections could be performed.

The dose of rAAV to be administered in methods disclosed herein will vary depending, for example, on the particular rAAV, the mode of administration, the treatment goal, the individual, and the cell type(s) being targeted, and may be determined by methods standard in the art. Titers of each rAAV administered may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$, about $1\times10^{14}$, or to about $1\times10^{15}$ or more DNase resistant particles (DRP) per ml. Dosages may also be expressed in units of viral genomes (vg) (i.e., $1\times10^7$ vg, $1\times10^8$ vg, $1\times10^9$ vg, $1\times10^{10}$ vg, $1\times10^{11}$ vg, $1\times10^{12}$ vg, $1\times10^{13}$ vg, $1\times10^{14}$ vg, $1\times10^{15}$ respectively). Methods for titering AAV are described in Clark et al., *Hum. Gene Ther.*, 10: 1031-1039 (1999).

Administration of an effective dose of the compositions may be by routes standard in the art including, but not limited to, intramuscular, parenteral, intravenous, oral, buccal, nasal, pulmonary, intracranial, intraosseous, intraocular, rectal, or vaginal. Route(s) of administration and serotype(s) of AAV components of rAAV (in particular, the AAV ITRs and capsid protein) of the invention may be chosen and/or matched by those skilled in the art taking into account the disease state being treated and the target cells/tissue(s) that are to express the ANO5 protein. In some embodiments, the route is one or more intramuscular injections into the quadriceps of the patient. In some embodiments, the route is one or more intramuscular injections into each of the three major muscle groups of the quadriceps of the patient.

In particular, actual administration of rAAV of the present invention may be accomplished by using any physical method that will transport the rAAV recombinant vector into the target tissue of an animal. Administration according to the invention includes, but is not limited to, injection into muscle, the bloodstream and/or directly into the liver. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703, the disclosure of which is incorporated by reference herein. Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The rAAV can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as hydroxpropylcellulose. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Transduction with rAAV may also be carried out in vitro. In one embodiment, desired target muscle cells are removed from the subject, transduced with rAAV and reintroduced into the subject. Alternatively, syngeneic or xenogeneic muscle cells can be used where those cells will not generate an inappropriate immune response in the subject.

Suitable methods for the transduction and reintroduction of transduced cells into a subject are known in the art. In one embodiment, cells can be transduced in vitro by combining rAAV with muscle cells, e.g., in appropriate media, and screening for those cells harboring the DNA of interest using conventional techniques such as Southern blots and/or PCR, or by using selectable markers. Transduced cells can then be formulated into pharmaceutical compositions, and the composition introduced into the subject by various techniques, such as by intramuscular, intravenous, subcutaneous and intraperitoneal injection, or by injection into smooth and cardiac muscle, using e.g., a catheter.

Transduction of cells with rAAV of the invention results in sustained expression of ANO5 protein. The present invention thus provides methods of administering/delivering rAAV which express ANO5 to an animal, preferably a human being. These methods include transducing tissues (including, but not limited to, tissues such as muscle, organs such as liver and brain, and glands such as salivary glands) with one or more rAAV of the present invention. Transduction may be carried out with gene cassettes comprising tissue specific control elements. For example, one embodiment of the invention provides methods of transducing muscle cells and muscle tissues directed by muscle specific control elements, including, but not limited to, those derived from the actin and myosin gene families, such as from the myoD gene family [See Weintraub et al., Science, 251: 761-766 (1991)], the myocyte-specific enhancer binding factor MEF-2 [Cserjesi and Olson, Mol Cell Biol 11: 4854-4862 (1991)], control elements derived from the human skeletal actin gene [Muscat et al., Mol Cell Biol, 7: 4089-4099 (1987)], the cardiac actin gene, muscle creatine kinase sequence elements [See Johnson et al., Mol Cell Biol, 9:3393-3399 (1989)] and the murine creatine kinase enhancer (mCK) element such as the MCK7 or tMCK which is triple copies of the mouse mCK, control elements derived from the skeletal fast-twitch troponin C gene, the slow-twitch cardiac troponin C gene and the slow-twitch troponin I gene: hypozia-inducible nuclear factors (Semenza et al., Proc Natl Acad Sci USA, 88: 5680-5684 (1991)), steroid-inducible elements and promoters including the glucocorticoid response element (GRE) [See Mader and White, Proc. Natl. Acad. Sci. USA 90: 5603-5607 (1993)], and other control elements.

Muscle tissue is an attractive target for in vivo gene delivery and gene therapy, because it is not a vital organ and is easy to access. The invention contemplates sustained expression of biologically active ANO5 proteins from transduced myofibers.

By "muscle cell" or "muscle tissue" is meant a cell or group of cells derived from muscle of any kind (for example, skeletal muscle and smooth muscle, e.g. from the digestive tract, urinary bladder, blood vessels or cardiac tissue). Such muscle cells may be differentiated or undifferentiated, such as myoblasts, myocytes, myotubes, cardiomyocytes and cardiomyoblasts. Since muscle tissue is readily accessible to the circulatory system, a protein produced and secreted by muscle cells and tissue in vivo will logically enter the bloodstream for systemic delivery, thereby providing sustained, therapeutic levels of protein secretion from muscle.

The term "transduction" is used to refer to the administration/delivery of ANO5 DNA to a recipient cell either in vivo or in vitro, via a replication-deficient rAAV of the invention resulting in expression of a functional ANO5 protein by the recipient cell.

Antioxidant Compositions

The production of reactive oxygen species during skeletal muscle contraction is well established. During prolonged exercise, elevated amounts of these oxidants cause damage to proteins and lipids, and lead to activation of multiple stress response signaling pathways (Powers et al., Free Radic Biol Med 51: 942-50 (2011)). Consequently, several studies have investigated the use of long-term antioxidant supplementation as a means of alleviating oxidative stress in skeletal muscle. One recent study reported that a formulation of three antioxidants (vitamin E, α-lipoic acid, and coenzyme Q10) supplemented into the diet of female mice improved running performance, as well as markers of mitochondrial function (Abadi et al., PLoS One. 8:e60722 (2013)). However, others have reported that a similarly modified diet (vitamin E+α-lipoic acid) reduced mitochondrial biogenesis in rats (Strobel et al., Med Sci Sports Exerc. 43:1017-24 (2011)). Currently, there is no consensus in the art on the effect of long-term antioxidant supplementation on skeletal muscle health, and very little attention has been given to muscles weakened by disease. However, the invention provides evidence that an antioxidant diet provide beneficial effects on the skeletal muscle of Ano5$^{-/-}$ mice.

Antioxidants

The invention provides for the administration of an antioxidant composition to improve muscle physiology and function in subject suffering from muscular dystrophy. The antioxidant composition disclosed herein utilizes at least one antioxidant. In addition, the invention provides for antioxidant compositions that comprise at least two or at least three antioxidants, and in these compositions the antioxidants will have different cellular functions. Preferred antioxidants are those that have been shown to specifically reverse mitochondrial damage as a product of aging. For example, the invention provides for antioxidant compositions comprising at least one of co-enzyme Q10, α-lipoic acid, carotenoids (α-carotene, β-carotene, lycopene, lutein, astaxanthin, canthaxanthin and zeaxanthin), vitamins such as vitamin A (retinol, 3,4-didehydroretinol, and 3-hydroxyretinol), vitamin C (ascorbic acid), and vitamin E (α-tocopherol), vitamin cofactors, polyphenols and flavonoids (resveratrol, gingerol, curcumin), or Minerals (Iron, Magnesium, Selenium, Copper, Zinc, Manganese, Iodide). In preferred embodiments these antioxidants are coenzyme Q10, vitamin E, α-lipoic acid.

Coenzyme Q10, also known as Q10, vitamin Q10, ubiquinone, ubidecarenone or coenzyme Q, is a fat soluble substance. Coenzyme Q10 is an electron shuttling compound that is critical to the electron transport chain (ETC). The ETC drives ATP synthesis which is a vital source of energy for the cell. Vitamin E, also known as α-tocopherol, is an important component of membranes (including mitochondrial membranes) and functions to scavenge lipid free radicals.

α-Lipoic acid, also known as thioctic acid is an organosulfur compound derived from octanoic acid which is an essential cofactor for mitochondrial dehydrogenases such as pyruvate dehydrogenase for proper function of the Krebs cycle ultimately resulting in ATP production. α-Lipoic acid also has direct skeletal muscle effects by activating AMPK, an energy sensor in the cell that regulates mitochondrial biogenesis via PGC1α.

Polyphenols include phenolic acid and flavonoids. For example phenolic acids include protocatechuic acid, gallic acid, hydroxybenzoic acid, hydroxycinnamic acid such as caffeic acid, chlorogenic acid, coumaric acid, ferulic acid, sinapic acid, anthocyanins such as cyanidin, pelargonidin, peonidin, delphinidin and malvidin. Exemplary flavonoids include flavonols such as quercetin, kaempferol, myricetin, flavones such as apigenin and luteolin, glavaonones such as hesperetin, naringenin, and eriodictyol, isoflavones such as daidzein, genistein, and glycitein, and monomeric flavonols such as catechin and epicatechin.

Administration and Dosing

The present disclosure provides materials and methods for the treatment of muscular dystrophy and chronic muscle wasting using at least one, antioxidant. Exemplary compositions and methods of treating muscular dystrophy comprising administering at least one antioxidant, or administering at least two antioxidants or administering at least three antioxidants. For example, the invention provides antioxidant compositions comprising α-lipoic acid, coenzyme Q10 and α-tocopherol (also known as vitamin E). In some embodiments, the antioxidant composition disclosed herein may be administered alone or in combination with AAV vectors comprising a nucleotide sequence encoding the ANO5 protein or a functionally active fragment thereof.

Methods of the present disclosure are performed using any medically-accepted means for administering the agents directly or indirectly into a mammalian subject, including but not limited to injections, oral ingestion, intranasal, topical, transdermal, parenteral, inhalation spray, vaginal, or rectal administration. The term parenteral as used herein includes subcutaneous, intravenous, intramuscular, and intracisternal injections, as well as catheter or infusion techniques. Administration by, intradermal, intraperitoneal, intrathecal, retrobulbar, intrapulmonary injection and or surgical implantation at a particular site is contemplated as well.

In one embodiment, administration is performed at the affected tissue (e.g. muscle) needing treatment by direct injection into the site or via a sustained delivery or sustained release mechanism, which can deliver the formulation internally. For example, biodegradable microspheres or capsules or other biodegradable polymer configurations capable of sustained delivery of a composition (e.g., a soluble polypeptide, antibody, or small molecule) can be included in the formulations of the disclosure implanted near or at affected tissue.

In some embodiments, concurrent administration of antioxidants and AAV vectors comprising ANO5 does not require that the agents be administered at the same time or by the same route, as long as there is an overlap in the time period during which the agents are exerting their therapeutic effect. Simultaneous or sequential administration is contemplated, as is administration on different days or weeks.

In some embodiments, antioxidants and/or AAV vector compositions may also be delivered to the patient at multiple sites. The multiple administrations may be rendered simultaneously or may be administered over a period of time. In certain cases it is beneficial to provide a continuous flow of the therapeutic composition. Additional therapy may be administered on a period basis, for example, hourly, daily, every other day, twice weekly, three times weekly, weekly, every 2 weeks, every 3 weeks, monthly, or at a longer interval.

It is contemplated the agents of the present disclosure may be given simultaneously, in the same formulation. It is further contemplated that the agents are administered in a separate formulation and administered concurrently, with concurrently referring to agents given within 30 minutes of each other.

Thus, the invention provides methods of administering an effective dose (or doses, administered essentially simultaneously or doses given at intervals) of rAAV that encode, for example, ANO5 and/or antioxidants to a patient in need thereof.

The amounts antioxidants compositions in a given dosage may vary according to the size of the individual to whom the therapy is being administered as well as the characteristics of the disorder being treated. In exemplary treatments, it may be necessary to administer an antioxidant diet comprising about 0.1%, 0.2%, 0.3%, 0.4%, 0.5%. 0.6%, 0.7%, 0.8%, 0.9%, 1.0% lipoic acid, about 0.1%, 0.2%, 0.3%, 0.4%, 0.5%. 0.6%, 0.7%, 0.8%, 0.9%, 1.0% coenzyme Q10 and about 10, 100, 200, 300, 400, 500, 600, 700, 800, 900, 1000, 2000, 3000, 4000, 5000 IU α-tocopherol or vitamin E. These concentrations may be administered as a single dosage form or as multiple doses. Standard dose-response studies, first in animal models and then in clinical testing, reveals optimal dosages for particular disease states and patient populations.

It will also be apparent that dosing may be modified if traditional therapeutics are administered in combination with therapeutics of the disclosure.

EXAMPLES

Example 1

Isolation and Generation of an Ano5−/− Mouse Model

An Ano5 knock-out model was generated using a vector targeting Ano5 from exon 8 to exon 9 to produce a truncated transcript as shown in FIG. 1A. The targeting construct was designed as a "knock-out first" conditional ready construct so that a null allele is generated through splicing to a lacZ trapping element as described Tesla et al. (*Genesis* 38, 151-158 (2004). This lacZ-tagged mutant allele Ano5:tm1a (KOMP)Wtsi targeting vector was obtained from the UC Davis KOMP Repository (PG00097_Z_1_G0; Karnes. *Nature* 474, 337-342 (2011). The targeting cassette was inserted following exon 8 with flanking FRT and loxP sites present to generate a conditional allele if embryonic lethality was noted.

Following embryonic stem cell targeting and transfer, the genotypes were verified by genomic PCR (FIG. 1b). Clones were screened by RT-PCR using the following primer sets spanning exons 1-6 (e1-6) or exons 17-20 (e17-20), which produced a 300 bp amplicon from the endogenous Ano5 locus and a 200 bp amplicon from the Ano5 cassette insertion locus, as shown in FIG. 1c:

```
genotyping F
                                       (SEQ ID NO: 3)
5'-AGTCCTTTTCAGCACAGTCTTTG-3' genotyping R
                                       (SEQ ID NO: 4)
5'-TGAGGCAGTGTGGAGTGAGTA-3'

DF38700
                                       (SEQ ID NO: 5)
5'-GCCAATCATATGGTCTCAGT-3'

LR-loxp R
                                       (SEQ ID NO: 6)
5'-ACTGATGGCGAGCTCAGACC-3'
```

Successfully targeted ES cells were then injected into blastocysts of C57BL/6 mice, and embryos transferred to generate chimeras for germline transmission. Transgenic heterozygotes were verified by genotyping and were backcrossed four times to C57BL/6 wild type, before breeding to homozygosity. Stocks of Ano5−/− and C57BL/6 mice were bred and maintained as homozygous animals in standardized conditions in the Vivarium at the RINCH. They were maintained on Teklad Global Rodent Diet (3.8% Fiber, 18.8% Protein, 5% fat chow) with a 12:12 h dark:light cycle.

Quantitative PCR was performed and analyzed on a Fast Real-Time PCR System (Thermo Fisher Scientific). Reactions were run with Applied Biosystems primer-FAM probe cocktails for Ano5 (Mm00624629_m1, Mm01335981_m1), Ano6 (Mm00614693_m1), and Gapdh (Mm99999915_g1), in triplicate for each sample. The ΔΔCt method was used to calculate normalized fold-change reductions of Ano5 and Ano6 mRNA in Ano5−/− muscles as compared to wild type.

Total RNA was isolated from fresh-frozen muscle shavings using Trizol (Life Technologies, Carslbad, Calif.), according to the manufacturer's protocol. RNA was then column-purified using the RNAEasy method (Qiagen, Valencia, Calif.), and quantified by spectrophotometry using a Nano-DropLite (Thermo Fisher Scientific, Waltham, Mass.). cDNA was generated with the High Capactiy cDNA Reverse Transcription Kit (Thermo Fisher Scientific), using equivalent amounts of sample RNA per reaction (200-500 ng). For semi-quantitative PCR, equal volumes of cDNA were subjected to 30 PCR cycles, followed by agarose gel electrophoresis. Primers used were:

```
mβACt-rt-5'
                                     (SEQ ID NO: 7)
CCTGGCCGTCAGGCAGAT mβAct-rt-3'
                                     (SEQ ID NO: 8)
GACATGGAGAAGATCTGGCACC mAno5-rt-F1
                                     (SEQ ID NO: 9)
CCAACAGAATGAGAACCT mAno5-rt-R1
                                     (SEQ ID NO: 10)
GACAGGGGTGGGTACTTTGG mAno5-rt-F3
                                     (SEQ ID NO: 11)
CGTTGGCAGCAAGATCAT mAno5-rt-R3
                                     (SEQ ID NO: 12)
GGGTACCTATAATCTCTGTACCTGC
```

Quantitative RT-PCR demonstrated-80% reduction in pre-cassette transcript and >99% reduction of post-cassette ANO5 transcript in all muscles tested (FIG. 1d). No embryonic lethality or difficulty breeding was noted. As Ano5 shares a significant sequence homology to Ano6, and Ano6 is known to be expressed in skeletal muscle under some conditions, RT-PCR was performed to measure relative expression of ANO6 cDNA of Ano5$^{-/-}$ mouse muscles. Quantitative RT-PCR demonstrates a modest, but statistically insignificant elevation of Ano6 transcript in Ano5 deficient muscles.

Example 2

Clinical and Histopathological Evaluation of the Ano5$^{-/-}$ Mouse

Figure 2:
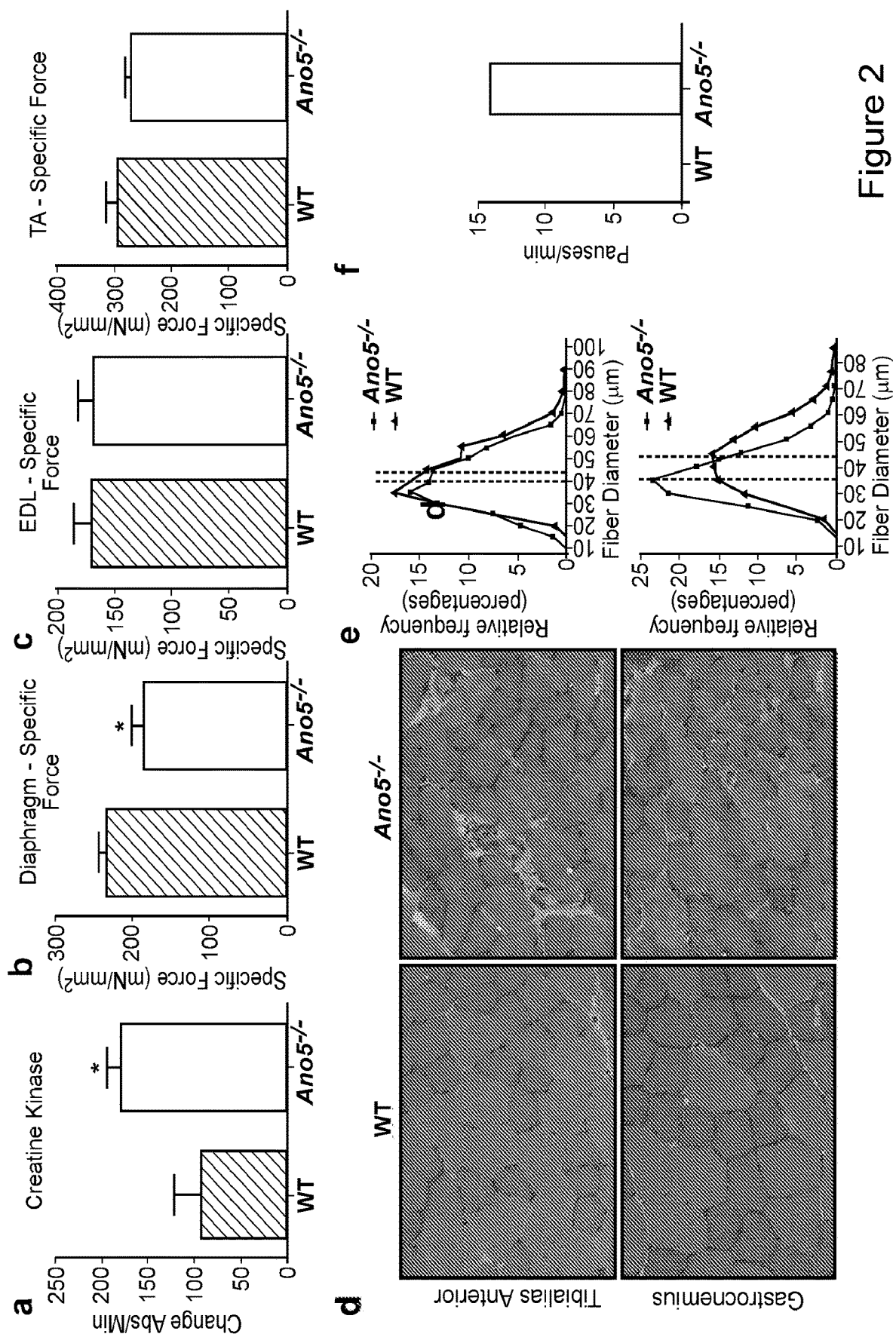
FIG. 2A-2F illustrates the characterization of Ano5-/- deficient mice. Panel (a) demonstrates that serum creatine kinase is significantly elevated in Ano5-/- mice at 9 months (P<0.05, t-test). Panel (b) demonstrates specific force of contraction of diaphragm strips from 9 months old Ano5-/- mice was significantly decreased compared to controls (P<0.01, t-test). Panel (c) demonstrates that the specific force of contraction of EDL and tibialis anterior (TA) muscles from 9 month Ano5-/- mice were not significantly different than controls (P>0.05, t-test). Panel (d) depicts hematoxylin and eosin stained tissue sections demonstrating mild dystrophic pathology including central nuclei, fiber size variability, and areas of necrosis in the TA and GAS of the Ano5-/- mouse compared to WT controls. Scale Bar=50 µm. Panel (e) provides muscle fiber diameter measurements showing a reduction in fiber diameter size compared to WT, especially in GAS muscle (P<0.0001, t-test). Panel (f) exhibits that Ano5-/- mice demonstrated frequent pauses when treadmill exhaustion studies were performed.

The Ano5$^{-/-}$ mouse exhibited many features characteristic of human ANO5-myopathy including increased serum creatine kinase levels, variable weakness among muscles, altered muscle fiber diameter, and exercise intolerance. Serum creatine kinase is elevated approximately 2-fold in Ano5$^{-/-}$ mice (FIG. 2a).

Tetanic force measurements were obtained from extensor digitorum longus (EDL) of 10 month old mice (n=6 mice per strain), tibialis anterior (TA) from 4 month old mice (n=5 mice per strain), and diaphragm muscles of 10 month old Ano5$^{-/-}$ and WT mice (n=4 mice per strain). The EDLs were dissected at the tendons and subjected to a physiology protocol to assess function as previously described by Rodino-Klapac et al. (J. Transl. Med. 5: 45, 2007) and Liu et al. (Mol. Ther. 11:245-256, 2005) with modifications. During the eccentric contraction protocol, a 5% stretch-re-lengthening procedure executed between 500 and 700 ms (5% stretch over 100 ms, followed by return to optimal length in 100 ms). Following the tetanus and eccentric contraction protocol, the mice were then euthanized and the muscle was disssected, wet-weighed, mounted on chuck using gum tragacanth, and then frozen in methyl-butane cooled in liquid nitrogen. Force measurements in the TA were performed as described by Hakim et al. (J. Appl. Physiol. 110: 1656-1663, 2011) and Wein et al. (Nat. Med. 20:992-1000, 2014).

For diaphragm force measurements, mice were euthanized and the diaphragm was dissected with rib attachments and central tendon intact, and placed in Krebs-Henselet (K-H) buffer as previously described by Beastrom et al. (Am. J. Pathol. 179: 2464-2474, 2011), Rafeal-Fortney et al. Circ. 124: 582-588, 2011) and Grose et al. (Ann. Clin. Trans. Neurol. 1: 34-44, 2014). A 2-4 mm wide section of diaphragm was isolated. Diaphragm strips were tied firmly with braided surgical silk (6/0; Surgical Specialties, Reading, Pa.) at the central tendon, and sutured through a portion of rib bone affixed to the distal end of the strip. Each muscle was transferred to a water bath filled with oxygenated K-H solution that was maintained at 37° C. The muscles were aligned horizontally and tied directly between a fixed pin and a dual-mode force transducer-servomotor (305C; Aurora Scientific, Aurora, Ontario, Canada). Two platinum plate electrodes were positioned in the organ bath so as to flank the length of the muscle. The muscle was stretched to optimal tension of 1 g, and then allowed to rest for 10 minutes before initiation of the tetanic protocol. Once the muscle was stabilized, the muscle was subjected to a warm-up consisting of three 1 Hz twitches every 30 seconds followed by three 150 Hz twitches every minute. After a 3 minute rest period, the diaphragm was stimulated at 20, 50, 80, 120, 150, 180 Hz, allowing a 2 minute rest period between each stimulus, each with a duration of 250 ms to determine maximum tetanic force. Muscle length and weight was measured. The force was normalized for muscle weight and length (CSA: muscle mass (mg)/{Lf (mm)× muscle density (1.06 mg/mm$^3$)}). Statistical significance was assessed using an unpaired Student's T-test for specific force and 2-way ANOVA with repeated measurements for resistance to eccentric contraction protocol.

The specific force of muscle contraction was significantly decreased ~15% in diaphragm (FIG. 2b), but was essentially unaffected in extensor digitorum longus (EDL) and tibialis anterior (TA) muscles (FIG. 2c) of the Ano5'-mice. This variability among muscles is characteristic of ANO5 myopathies and was also observed in histological analysis of different muscles. Relative to wild type (WT), average muscle fiber diameter was significantly smaller in gastrocnemius (GAS) muscle from Ano5$^{-/-}$ mice (Ano5$^{-/-}$ 35.8±8.3 µm, WT: 41.8±11.0 µm, P<0.001), and to a lesser extent in the TA muscle (Ano5$^{-/-}$ 38.1±11.8 µm, WT: 44.3±12.2 µm, P<0.001) (FIG. 2d,e). Ano5'-muscles exhibited mild histopathology including central nuclei and occasional necrotic fibers (FIG. 2d,e).

To evaluate exercise tolerance, 7.5 month old aged-matched Ano5$^{-/-}$ and WT mice were subjected to exercise regimes weekly for 1 hour for 2 months. Each mouse was run once a week at a −10° decline with a speed of 15 m/min and increased by 1 m every minute until exhaustion was reached (n=3 mice per strain). Each individual test was stopped when the mouse remained on the shock plate (Columbus Instruments) with electrical stimulus set to 20V for more than 10 seconds without attempting to engage in exercise. Breaks were defined as the times where the mice ceased running and rested while the treadmill belt returned to the shock plate. While WT control mice ran at a consistent speed with no breaks, Ano5$^{-/-}$ mice were prone to frequent breaks on the treadmill (14 pauses/min) where they ceased running until the treadmill belt returned to the shock plate (FIG. 2f).

Figure 3:
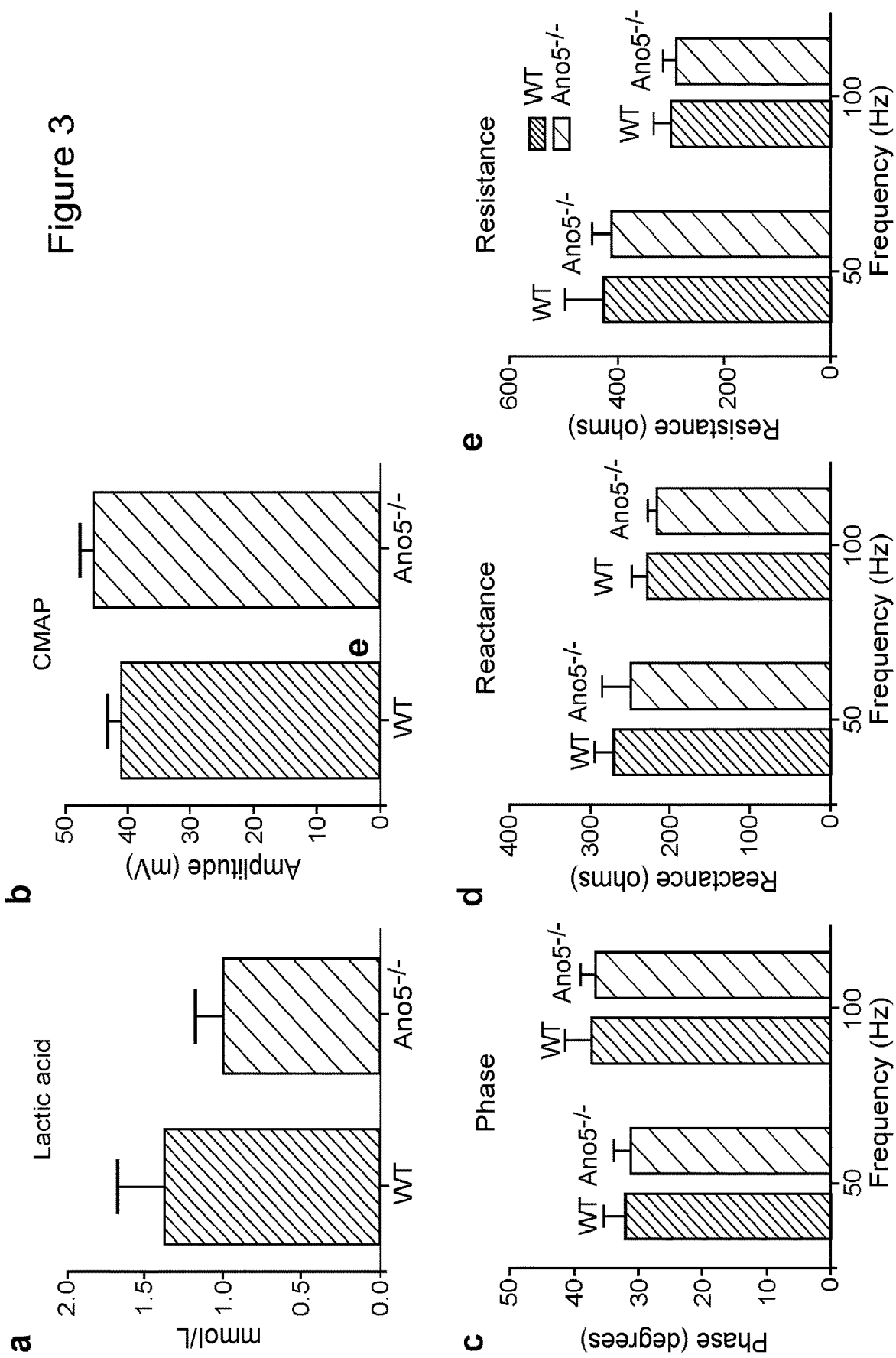
FIG. 3A-3E provides physiological characterization of Ano5$^{-/-}$ mice. Panel (a) Lactic acid levels were slightly reduced in Ano5-/- mice compared to WT controls following treadmill running (P=0.15). Panel (b) Electrophysiological characteristics of the muscle. CMAP amplitude was not significantly difference between Ano5$^{-/-}$ (45.1±2.2 mV) and WT (40.8±2.4 mV) (p=0.22). No Ano5-/- or WT animal demonstrated fibrillation potentials. Panels (c-e) Impedance characteristics of muscle at 50 kHz (phase; reactance; resistance, respectively). There were no differences between Ano5-/- (31.0±2.7; 248.1±37.8Ω; 411.4±34.6Ω) and WT fibers (31.7±3.9; 269.0±83.9Ω; 424.3±73.9Ω) (phase: p=0.59; reactance: p=0.44; resistance: p=0.59). No differences were observed at 100 kHz between Ano5-/- (36.5±2.4; 216.2±27.3Ω; 290.7±22.0Ω) and WT fibers (37.0±4.8; 228.4±63.9Ω; 295.8±36.1Ω) (phase: p=0.77; reactance: p=0.55; resistance: p=0.68).

Electrophysiology was performed on 6-8 mo Ano5$^{-/-}$ and control muscles using methods similar to those described in Arnold et al. (*Ann. Clin. Trans. Neurol.* 1:34-44, 2014). Mice were anesthetized using inhaled isoflurane and placed in the prone position with the hind limbs extended at 450 away from the body of the animal. Compound muscle action potential (CMAP) amplitudes were measured from bilateral triceps surae muscles following supramaximal sciatic nerve stimulation in mutant (n=6 animals, 12 hind limbs) and control (n=7 animals, 14 hind limbs) mice. Needle electromyography was performed in the right GAS muscle to assess for the presence or absence of fibrillation potentials. Localized impedance measures, or electrical impedance myography (EIM), was performed in bilateral GAS muscles at frequencies from 1000 Hz-10 MHz using a Skulpt Inc EIM1103 system (San Francisco, Calif.) using methods similar to those previously reported in mouse models of amyotrophic lateral sclerosis and muscular dystrophy (Li et al. *PLoS One* 8:e65976, 2013; Li et al. *Muscle & Nerve* 49: 829-835, 2014). A fixed electrode array with four 26 gauge insulated electromyography needle electrodes (Natus, Middleton, Wis.) spaced 1 mm apart was used in place of surface electrodes. The electrode array was inserted into the belly of bilateral gastrocnemius muscles in a longitudinal configuration in respect to muscle fiber direction, and two trials of impedance measurements were obtained in each muscle and averaged for a single value in each limb (n=6 animals, 12 hind limbs for each group). Using the convention from previously published EIM studies and for simplicity, reactance, resistance, and phase was analyzed at two current frequencies, 50 kHz and 100 kHz. CMAP amplitudes and impedance characteristics were compared using a two-tailed t test. Needle electromyography, evoked compound muscle action potential recordings, and electrical impedance myography were performed in the hindlimbs of Ano5$^{-/-}$ and WT mice but showed no significant changes, similar to the human disease (FIG. 3).

Another characteristic feature of human ANO5 myopathy is the presence of an excessive number of muscle fibers with intramuscular deposits. Muscle cross-sectional fiber diameters were determined from TA and gastrocnemius (GAS) muscles from 6 month old Ano5$^{-/-}$ and WT strain control mice (n=3 mice per strain). Muscles were sectioned and stained with hematoxylin and eosin (H&E). 4 random 20× images per section per animal were taken with a Zeiss AxioCam MRC5 camera. Fiber diameters were determined by measuring the shortest distance across the muscle fiber using Zeiss Axiovision LE4 software. Fiber diameter histograms were generated from an average of 500-600 fibers per TA and 600-700 fibers per GAS. An unpaired t-test was used to test significant differences between Ano5$^{-/-}$ and WT fiber sizes (****p<0.0001).

Aggregates within the muscles were quantitated. Muscle sections from TA and GAS muscles of 10 month old Ano5$^{-/-}$ and WT mice (n=3 mice per tissue and strain) were stained with Gomori Trichrome. Four 20× images were taken and the number of fibers with one or more aggregates were counted using Image J software and expressed as a percentage of the total number of fibers. Using GraphPad Prism, a one-way ANOVA was used to test significance between Ano5$^{-/-}$ and WT fibers (****p<0.0001).

In addition, succinate dehydrogenase staining (SDH) was carried out on the aggregates and muscle: Tibialis anterior (TA) and quadriceps muscles were sectioned at 18 m and stained with SDH solution consisting of 0.2% nitro blue tetrazolium (NBT) dissolved in 0.1 M succinic acid and 0.1 M phosphate buffer pH 7.4 and incubated at 37° C. for 3 hrs. Following incubation, slides were rinsed with water and dehydrated in serial alcohols then cleared with xylene. Slides were imaged on Zeiss AxioCam MRC5 camera.

Segments of TA muscle from 4 and 10 month old Ano5$^{-/-}$ and control mice were removed, stretched to their in situ length across a wooden tongue depressor and immersed in 3% glutaraldehyde in 0.1 M phosphate buffer pH 7.0 for 4 hours. The muscle was dissected into 2-mm-long tissue blocks, stored in 0.1 M phosphate buffer pH 7.4 overnight, followed by post-fixation in 1% osmium tetroxide for 2 hours and dehydration in graded ethanol solutions before plastic embedding. 1 µm-thick cross sections were stained with toluidine blue, examined by light microscopy, and tissue sections from selected blocks were examined under a Hitachi H-7650 TEM electron microscope utilizing an Advanced Microscopy Techniques camera and software.

Figure 4:
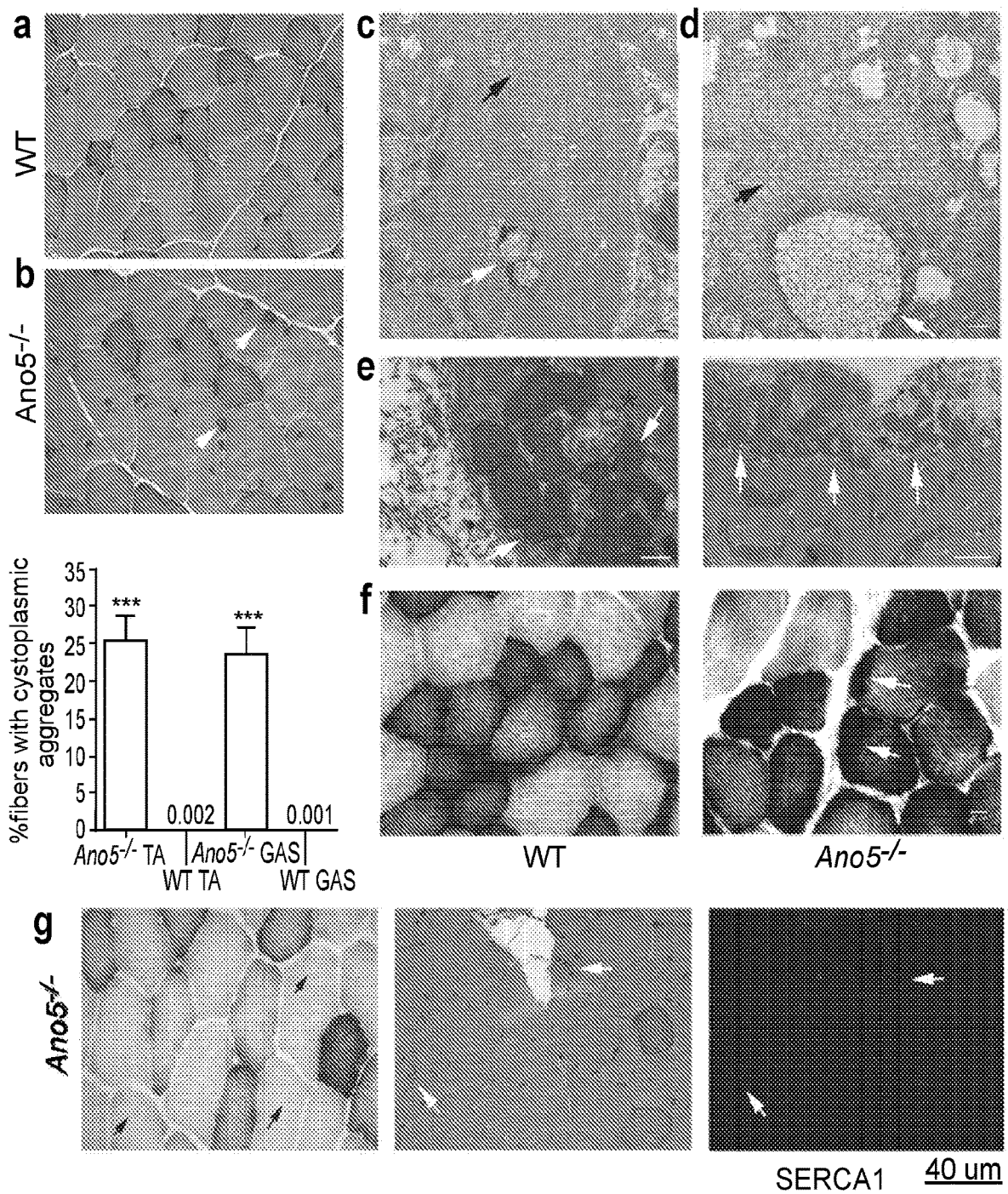
FIG. 4A-4G provides subcellular histopathology in Ano5$^{-/-}$ muscle. Panel (a) provides Gomori Trichrome stain of 10 mo Ano5$^{-/-}$ and WT TA muscles. Ano5$^{-/-}$ muscle contains membrane aggregates (arrows). Scale Bar=20 µm Panel (b) provides quantification of the number of fibers containing aggregates in TA and GAS muscles of the Ano5$^{-/-}$ compared to WT (p<0.0001, one-way ANOVA). Panels (c,d) provide electron microscopic images demonstrating the presence of membrane aggregates in Ano5$^{-/-}$ muscle. Aggregates were either loosely packed, interconnecting tubular formations with fuzzy inner tubules (white arrows) or densely packed accumulations of vesicular or tubular membranes (black arrows). Scale bars=500 nm. Panel (e) demonstrates sub-sarcolemmal accumulations of mitochondria (arrows) and degenerating mitochondria (asterisk) were frequently identified by electron microscopy in Ano5$^{-/-}$ muscle. Scale bars=500 nm (left) and 2 µm (right). Panel (f) provides succinate dehydrogenase staining of 10 mo Ano5$^{-/-}$ TA muscle showed sarcolemmal thickening and capped fibers that were not present in WT. Scale bars=10 µm. Panel (g) provides cryosections of the TA muscle from 10 mo Ano5$^{-/-}$ mice were stained for succinate dehydrogenase (SDH). Arrows indicate aggregates that do not stain for SDH (left). Serial sections from 10 mo Ano5$^{-/-}$ mice demonstrate that many membrane aggregates (white arrows) observed with trichrome staining are positive for SERCA1 (right) suggesting they are derived from the sarcoplasmic reticulum. Scale Bar=40 µm.

In the Ano5−/− mouse muscle, these structures appear as sharply-defined, irregularly-contoured areas that stain red with a modified trichrome stain as described in Pavlocicova et al. (*Gen. Physiol. Biophysics* 22: 425-440, 2003). Cytoplasmic aggregates were apparent beginning at 9 months of age and increased over time (FIG. 4a). Because aggregates of similar appearance have been noted in normal aged mice, aggregate occurrence was quantified. Approximately 25% of Ano5$^{-/-}$ fibers displayed irregularly-contoured red areas upon trichrome staining, while <0.02% of control fibers had these aggregates (FIG. 4b). Electron microscopy (EM) revealed that these aggregates were comprised of membranous material. Many Ano5' muscle fibers exhibited densely packed accumulations of vesicular or tubular membranes or haphazardly oriented and loosely packed interconnecting tubular formations with fuzzy inner tubules that corresponded to the aggregates seen in light microscopy (FIG. 4c,d). ANO5$^{-/-}$ mice showed similar pathology findings consistent with that of diagnosed ANO5 patients. Electron microscopy of patient muscle with compound heterozygous for two mutations [c. 155A>G (p.Asn52Ser)]+[c.191dupA (p.Asn64Lysfs*15)] in the coding region of the ANO5 gene revealed numerous aggregates and multiple sites displaying areas of degenerating mitochondria. Aggregates in Ano5$^{-/-}$ muscle stained positive for SERCA1 but not for succinate dehydrogenase (SDH) activity, suggesting that they are derived from the sarcoplasmic reticulum and not from mitochondria (FIG. 4g). However, Ano5$^{-/-}$ mice did exhibit degenerating mitochondria and sub-sarcolemmal mitochondrial accumulation in addition to these membrane aggregates (FIG. 4e). The sub-sarcolemmal accumulation of mitochondria was confirmed by staining frozen sections for SDH, which was localized in dense patches near the surface of muscle fibers (FIG. 4f). To identify whether the mitochondrial degeneration observed had functional significance, citrate synthase activity was quantified as a measure of intact mitochondria and demonstrated that there was a significant decrease in Ano5$^{-/-}$ muscle extracts compared to WT controls Example 3

Ano5 Facilitates Membrane Repair

In healthy individuals, normal exercise results in small lesions in the plasma membrane that are healed by two processes: (i) small tears are resealed by assembly of new plasma membrane and (ii) sites of more severe disruption are repaired by satellite cells that differentiate into myoblast-like cells and fuse to regenerate multinucleated muscle fibers. To test the effect of loss of ANO5 expression on membrane repair, the effect of membrane damage produced by an intense laser pulse delivered to isolated flexor digitorum brevis (FDB) muscle fibers was examined. 12 m cryosections were placed onto Fisher Superfrost microscope slides and blocked with 10% goat serum and 0.1% Tween-20 in PBS for 1 hour at room temperature. Slides were incubated in primary antibody for 1 hour at room temperature (Anti-FLAG F7425 Sigma-Aldrich, 1:175), Sercal CaF2-5D2 (Developmental Studies Hybridoma Bank, 1:50). Slides were then rinsed 3 times with PBS for 1 hour at room temperature followed by a 30 min block. Goat-anti-mouse conjugated to Alexa Fluor 594 (A21125, Life Technologies) or goat-anti-rabbit conjugated to Alexa Fluor 568 (A11011, Life Technologies) secondary antibodies were diluted at 1:250 in blocking solution and incubated for 45 min followed by 3 PBS rinses for 1 hour. The sections were mounted with Vectashield (Vector Labs, Burlingame, Calif.) mounting media and analyzed with a Zeiss Axioskop 2 microscope using a Cy5 filter (excitation, 578 nm-590 nm; emission 603 nm-671 nm) (Zeiss, Thornwood, N.Y.). Image exposure time was standardized using the positive control for each antibody, each day. Images were taken using the Axiovision 4.5 software.

Figure 5:
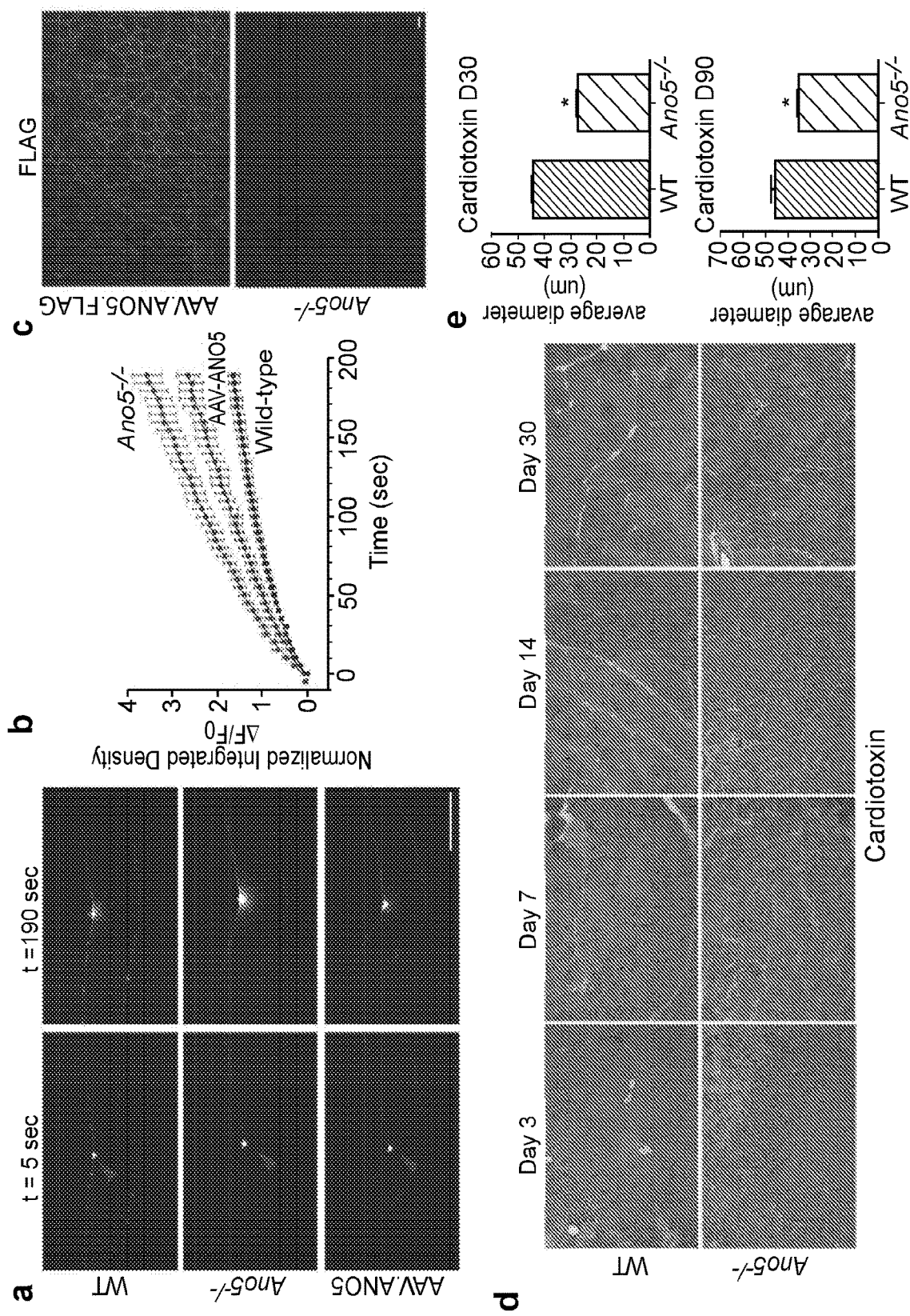
FIG. 5A-5E demonstrates that membrane repair is defective in Ano5$^{-/-}$ mice. Panel (a) provides images of Ano5$^{-/-}$ and WT muscle fibers damaged by a laser pulse shown 5 sec and 190 sec post-injury. Red arrows indicate the site of damage with FM1-43 dye accumulating quickly in Ano5$^{-/-}$ muscle compared to WT. Scale Bar=50 µm. Panel (b) provides measurement of fluorescence intensity after laser-induced injury. Ano5$^{-/-}$ muscle is statistically different from WT and AAV.ANO5 fibers at all times >100 seconds post-injury (2-way ANOVA, P<0.001). Panel (c) exhibits expression of ANO5-FLAG in Ano5$^{-/-}$ muscles injected with 5×10$^{10}$ vg AAV.ANO5.FLAG vector. Immunofluorescence with anti-FLAG antibody demonstrated ANO5-FLAG expression at the cell surface in treated muscle (top) that was absent in untreated Ano5$^{-/-}$ muscle (bottom). Scale bar=40 µm Panel (d) demonstrates recovery from cardiotoxin-induced muscle damage. Hematoxylin and eosin stained tissue sections of WT and Ano5$^{-/-}$ TA muscles at 1, 3, 7, 14, 30 and 90 days post cardiotoxin injection (d 3,7,14 and 30 shown). Ano5$^{-/-}$ muscle incurred more damage and showed an impairment in regeneration compared to WT. Panel (e) demonstrates myofiber size remains statistically smaller in Ano5$^{-/-}$ muscle compared to WT at 30 d (Cardiotoxin D30) and 90 d (Cardiotoxin D90) post cardiotoxin injection (P<0.05, t-test).

Membrane damage was assessed by accumulation of FM1-43, a membrane-impermeant styryl cationic dye that is not fluorescent in aqueous solution but fluoresces brightly in a lipid environment and has been used extensively to study membrane repair. A small area of fluorescence was detected at the site of damage in WT and Ano5$^{-/-}$ fibers immediately after laser injury (FIG. 5a). The increase in fluorescence was greater and occurred at a ~2-fold faster initial rate in Ano5$^{-/-}$ muscle fibers than in WT fibers. Whereas the fluorescence appeared to be leveling off at 190 sec in WT, the fluorescence continued to increase in Ano5$^{-/-}$ fibers for the duration of the experiment (FIG. 5b).

To test whether the defect in membrane repair was directly related to ANO5 expression, the human ANO5 cDNA was expressed using adeno-associated virus (AAV) in the Ano5$^{-/-}$ muscles (FIG. 4b,c). The human ANO5 cDNA (SEQ ID NO: 1) was cloned into an AAV2 ITR plasmid using Notl restriction sites between the MHCK7 promoter and polyadenlylation signal. rAAV vectors were produced by a modified cross-packaging approach whereby the AAV type 2 ITRs can be packaged into multiple AAV capsid serotypes as described in Rabinowitz et al. (*J. Virol.* 76: 791-801, 200). Production was accomplished using a standard 3-plasmid DNA CaPO$_4$ precipitation method using HEK293 cells. HEK293 cells were maintained in DMEM supplemented with 10% Cosmic calf serum (CCS, Hyclone). The production plasmids were: (i) pAAV.MHCK7.ANO5, (ii) rep2-cap8 modified AAV helper plasmids encoding cap serotype 8-like isolate rh.74, and (iii) an adenovirus type 5 helper plasmid (pAdhelper) expressing adenovirus E2A, E4 ORF6, and VA I/II RNA genes. Vectors were purified from clarified HEK293 cell lysates by sequential iodixanol gradient purification and anion-exchange column chromatography using a linear NaCl salt gradient as previously described in Clark et al. (*Human Gene Ther.* 10: 1031-10398, 1999). A quantitative PCR-based titration method was used to determine an encapsidated vector genome (vg) titer utilizing a Prism 7500 Taqman detector system (PE Applied Biosystems, Carlsbad, Calif.).

AAV vector delivery through intramuscular injection to mouse muscle. Four-five week old Ano5$^{-/-}$ mice were treated by intramuscular injection of 1×10$^{11}$ vg of rAAVrh.74.MHCK7.huANO5.FLAG into TA (n=4) or FDB (n=4) muscles. TA muscles were harvested 4 weeks post injection and processed for histological and immunofluorescent examination.

Flexor digitorum *brevis* (FDB) muscle fibers were harvested 10 weeks post treatment and subjected to a laser-induced injury. Membrane repair assay was performed on left and right FDB muscles of Ano5−/− (n=4) and age-matched C57BL6 (n=4) mice as described by Sondergaard et al. (Ann. Clin. Trans. Neurol. 2:256-270, 2015). Briefly, FDB fibers were isolated using a solution containing 2% w/v collagenase type I suspended in DMEM. Following dissociation of the muscle, fibers were placed in a glass bottom dish holding 2.5 µM FM1-43 dye in Dulbecco's PBS (no Ca/Mg) supplemented with 1.5 mM Ca2+. Fibers were subjected to laser injury using a FluoView® FV1000 two-photon confocal laser-scanning microscope (Olympus). Fibers were damaged with an 850 nm laser-guided spot of 4.479 mm at 20% power and imaged every 5 sec for 190 s to visualize FM1-43 dye uptake. An average of 7-10 fibers were imaged per muscle per mouse, (total 31 WT, 39 Ano5−/−, and 30 AAV-ANO5 rescued Ano5−/− fibers). Fluorescence intensity of dye infiltration surrounding the damage site on the membrane was analyzed with Image J software by measuring integrated density of pixel intensity within the defined area. To do so, under a 2× zoom setting on ImageJ, a rectangular box measuring 0.75 pixels by 1.00 pixel is drawn and used to measure the intensity of dye in that region. In the analysis, measured fluorescent intensity at an individual time point was normalized to initial intensity measured at t=−5 s (pre-injury). When fluorescence intensity was analyzed, values from all fibers from each strain were averaged together. A 2-way ANOVA was performed to determine statistical significance between treated and untreated fibers at each time point (p<0.001). To quantify the change in fluorescence, the data points were fit to the Hill equation using Origin Pro 9.1. All curves were fit with adjusted R2>0.998. Ano5−/− fibers, WT fibers, and AAV.ANO5 treated Ano5−/− fibers were significantly different beginning at 100 seconds post-injury. AAV.ANO5 partially restored membrane resealing in Ano5−/− muscle (FIG. 5a,b,c).

Example 4

Impaired Regeneration in Ano5 KO Mice

Investigation of whether muscle regeneration was also defective in Ano5$^{-/-}$ mice was carried out by examining the ability of the muscle to recover from injury produced by cardiotoxin injection (FIG. 5d). Mice were anesthetized with inhaled isoflurane and injected with cardiotoxin (diluted to 10 µM with sterile saline) every two weeks, for a total of 3 rounds. 30 µL and 50 µL of cardiotoxin was injected into the left TA and left GAS muscles respectively of 8 week old Ano5$^{-/-}$ and aged-matched controls. Sterile saline was injected into contralateral muscle as a sham control. Groups of mice were euthanized and their muscles harvested at 1, 3, 7 and 14, 30 and 90 days post final injection of cardiotoxin (n=3 mice per strain per timepoint). Four 20× images per TA were imaged and fiber diameter was measured on H&E-stained cryosections 1 and 3 months after the final cardiotoxin injection using Axio Vision 4.8. An average of 500-600 muscle fibers were measured and an unpaired t-test was performed (GraphPad Prism) to determine statistical significance between muscle fiber size of injured Ano5$^{-/-}$ mice and injured control mice (****p<0.0001).

To track temporal changes of necrosis and regeneration, TA and GAS muscles of 8 week-old mice were injected with cardiotoxin 3 times spaced 2 weeks apart. Tissues were harvested 1, 3, 7, 14, 30, and 90 d after the final injection (FIG. 5d). The contralateral side was used as a saline-only control. The WT muscle regenerated after cardiotoxin treatment, so that by 1 month the muscle appeared largely normal with the exception of central nuclei in newly regenerated fibers. However, in Ano5$^{-/-}$ mice, there was an extensive delay in regeneration and longstanding necrosis. After 3 months, the mean fiber diameter of Ano5$^{-/-}$ muscle remained significantly reduced compared to WT and many fibers exhibited central nuclei (FIG. 5d,e).

Example 5

Assessing the Effect of Antioxidant Therapy

To examine the potential benefits of a triple antioxidant diet on the skeletal muscle of Anoctamin 5 deficient (Ano5-/-) mice, cohorts of 2 month old wild type (WT) BL6 mice and Ano5-/- mice were fed either normal mouse chow or a diet supplemented with a triple antioxidant composition comprising 1000 IU vitamin E, 0.1% α-lipoic acid, and 0.25% coenzyme Q10 (in reduced ubiquinol form). Mice were run to exhaustion for 3 consecutive days every 4$^{th}$ week for a period of 16 weeks, and sacrificed to examine functional outcome measures associated with muscle health (activity and diaphragm force) and oxidative stress (citrate synthase activity and pgc1α expression).

Laser Monitoring of Open Field Cage Activity

An open-field activity chamber was used to determine overall activity of experimental mice following a previously described protocol (Kobayashi et al., *Nature* 456: 511-5 (2008); Beastrom et al., *Am J Pathol* 179: 2464-74 (2011)) with several modifications. All mice were tested at the same time of day in the early morning near then end of the night cycle when mice are most active. All mice were tested in an isolated room, under dim light and with the same handler each time. Also, as was done in the previous reports to reduce anxiety and keep behavioral variables at a minimum, which could potentially affect normal activity of the mice and consequently the results of the assay, we tested mice that were not individually housed (Voikar et al., *Genes Brain Behav* 4: 240-52(2005)). Mice were activity monitored using the Photobeam Activity System (San Diego Instruments, San Diego, Calif.). This system uses a grid of invisible infrared light beams that traverse the animal chamber front to back and left to right to monitor the position and movement of the mouse within an X-Y-Z plane. Activity was recorded for 1 hour cycles at 5-minute intervals. Mice were acclimatized to the activity test room for an initial 1 hour session several days prior to beginning data acquisition. Mice were tested in individual chambers in sets of 4. Testing equipment was cleaned between each use to reduce mouse reactionary behavioral variables that could alter our results. Data collected was converted to a Microsoft Excel worksheet and all calculations were done within the Excel program. Individual beam breaks for movement in the X and Y planes were added up for each mouse to represent total ambulation, and beam breaks in the Z plane were added up to obtain vertical activity within the 1 hour time interval.

Figure 6:
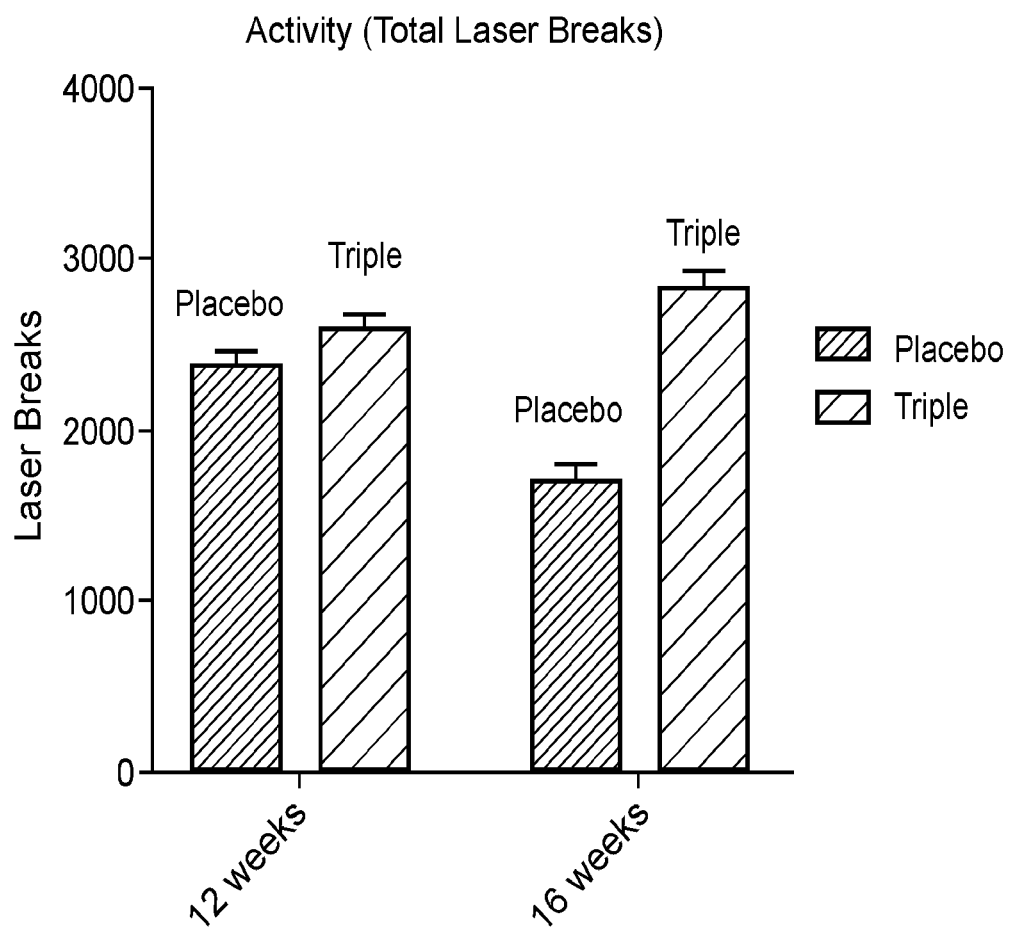
FIG. 6 demonstrates the voluntary activity for Ano5$^{-/-}$ mice treated with antioxidant therapy or placebo diet. The graph shows the voluntary activity (number of times mice broke horizontal and/or vertical laser beams in a 45 minute period) for Ano5$^{-/-}$ mice receiving antioxidant diet or placebo control for 12 and 16 weeks. Ano5$^{-/-}$ mice treated with triple antioxidant therapy has significantly increased activity compared to placebo treated at 16 weeks.

At the end of weeks 12 and 16, two mice from each group were placed in an activity cage to monitor voluntary activity. Total mouse activity was measured as the number of times mice broke horizontal and/or vertical laser beams in a 45 minute period following treadmill exhaustion (FIG. 6). Ano5$^{-/-}$ mice receiving the antioxidant diet were found to be more active than those on a standard (placebo) diet at 16 weeks, suggesting that the antioxidants had a positive effect on voluntary activity following exhaustion.

Diaphragm Tetanic Contraction for Functional Assessment

While behavioral assays were suggestive of some treatment effect, these outcome measures are subject to several variables independent of diet. To examine impact of antioxidant supplementation on skeletal muscle function, force measurements were performed on the diaphragm of mice Ano5-/- and WT mice (FIG. 7). The diaphragm was chosen because it was previously demonstrated that Ano5-/- mice have a deficit in diaphragm force, but not in limb muscles (Griffin et al., *Hum Mol Genet* 25: 1900-1911 (2016)).

Mice were euthanized and the diaphragm was dissected with rib attachments and central tendon intact, and placed in K-H buffer as previously described (Beastrom et al., *Am J Pathol* 179: 2464-74 (2011); Rafael-Fortney et al., *Circulation* 124: 582-8 (2011); Moorwood et al., *Journal of Visualized Experiments* 71: e50036 (2013)). A 2-4 mm wide section of diaphragm was isolated. Diaphragm strips were tied firmly with braided surgical silk (6/0; Surgical Specialties, Reading, Pa.) at the central tendon, and sutured through a portion of rib bone affixed to the distal end of the strip. Each muscle was transferred to a water bath filled with oxygenated K-H solution that was maintained at 37° C. The muscles were aligned horizontally and tied directly between a fixed pin and a dual-mode force transducer-servomotor (305C; Aurora Scientific, Aurora, Ontario, Canada). Two platinum plate electrodes were positioned in the organ bath so as to flank the length of the muscle. The muscle was stretched to optimal length for measurement of twitch contractions, and then allowed to rest for 10 minutes before initiation of the tetanic protocol. Once the muscle was stabilized, the muscle was set to an optimal length of 1 g and is subjected to a warm-up which consists of three 1 Hz twitches every 30 seconds followed by three 150 Hz twitches every minute. After a 3 min rest period, the diaphragm was stimulated at 20, 50, 80, 120, 150, 180 Hz, allowing a 2 min rest period between each stimulus, each with a duration of 250 ms to determine maximum tetanic force. Muscle length and weight was measured. The force was normalized for muscle weight and length. A significant improvement in diaphragm specific force was observed in triple antioxidant-treated ano5$^{-/-}$ mice compared to placebo-treated ano5' mice (FIG. 7).

Mitochondrial Biogenesis

Having established a connection with triple antioxidant therapy and oxidative fiber content, mitochondrial biogenesis and function was analyzed. Previous studies have shown exercise to stimulate pathways leading to mitochondrial biogenesis, while antioxidant therapy decreases this signaling. Results on male gastrocnemius muscle tissue confirmed that antioxidant treatment reduced expression of the key regulator of mitochondrial biogenesis PGC-1a (FIG. 8a). Interestingly, citrate synthase activity was found to be higher in antioxidant-fed mice among all genotype-gender combinations (FIG. 8b). One simple explanation for this is that the increased proportion of oxidative fibers, which are high in mitochondrial content, masks any decrease in mitochondrial biogenesis per fiber.

In summary, triple antioxidant therapy was found to have a significant impact on some measures of muscle physiology & function, including voluntary activity, diaphragm strength, fiber size, fiber type composition, and mitochondrial enzyme activity. These results were found to be, in certain cases, gender specific. LGMD2L is gender specific with males more severely affected.

What is claimed:

1. A method of treating limb-girdle muscular dystrophy type 2L (LGMD2L) comprising administering to a subject in need thereof a therapeutically effective amount of recombinant AAV (rAAV) vector, wherein the rAAV vector comprises
a MHCK7 promoter operably linked to a nucleic acid sequence comprising the nucleic acid sequence of SEQ ID NO:1, wherein administration of the rAAV vector transduces a muscle cell of the subject to express the ANO5 protein,
wherein the subject has a recessive mutation in the ANO5 gene, and wherein administration of the rAAV at least partially restores membrane resealing in the transduced muscle cell.

2. The method claim 1 wherein the recombinant AAV vector of is AAV1, AAV2, AAV4, AAV6, AAV7, AAV8, AAV9, AAV10, AAV11, AAV12, AAV13, AAV rh.74 or any variants thereof.

3. The method of claim 1 further comprising the step of administrating a therapeutically effective amount of an antioxidant composition to a subject in need thereof.

4. The method of claim 3 wherein the antioxidant composition comprises at least one of a coenzyme Q10, lipoic acid, vitamin, carotenoid, vitamin cofactor, mineral, polyphenol, or flavonoid.

5. A method of treating limb-girdle muscular dystrophy type 2L (LGMD2L) comprising administering to a subject in need thereof a therapeutically effective amount of recombinant AAV (rAAV) vector, wherein the rAAV vector comprises
a MHCK7 promoter operably linked to a polynucleotide sequence encoding the amino acid sequence of SEQ ID NO: 2, wherein administration of the rAAV vector transduces a muscle cell of the subject to express the ANO5 protein,
wherein the subject has a recessive mutation in the ANO5 gene, and wherein administration of the rAAV at least partially restores membrane resealing in the transduced muscle cell.

6. The method of claim 5 wherein the recombinant AAV comprises a polynucleotide sequence of SEQ ID NO: 1.

7. The method claim 5 wherein the recombinant AAV vector of is AAV1, AAV2, AAV4, AAV6, AAV7, AAV8, AAV9, AAV10, AAV11, AAV12, AAV13, AAV rh.74 or any variants thereof.

8. The method of claim 5 further comprising the step of administrating administering a therapeutically effective amount of an antioxidant composition to a subject in need thereof.

9. The method of claim 8, wherein the antioxidant composition comprises at least one of a coenzyme Q10, lipoic acid, vitamin, carotenoid, vitamin cofactor, mineral, polyphenol, or flavonoid.

* * * * *

SEQUENCE LISTING

<160> NUMBER OF SEQ ID NOS: 13

<210> SEQ ID NO 1
<211> LENGTH: 2739
<212> TYPE: DNA
<213> ORGANISM: Homo sapiens

<400> SEQUENCE: 1

| | | | | | | |
|---|---|---|---|---|---|---|
| atgggcgacc | cggatctcct | ggaagtgttg | gcggaggaag | gggaaaaagt | caataagcat | 60 |
| atagactact | ctttccaaat | gagtgagcag | agcctgagca | gcagagagac | cagctttctc | 120 |
| atcaatgaag | aaacaatgcc | tgcaaagcga | ttcaatttgt | tcctgaggcg | gcggcttatg | 180 |
| tttcaaaaaa | atcagcaaag | caaagattct | atcttcttcc | gagatgggat | taggcaaatt | 240 |
| gattttgtgc | tttcctacgt | tgatgacgta | aagaaagacg | cagagttaaa | ggcggaaaga | 300 |
| agaaaagagt | ttgaaactaa | tctcagaaaa | acaggtcttg | agttggaaat | agaagacaaa | 360 |
| agggactcgg | aagatggaag | aacttatttt | gtcaagatcc | atgcccttg | ggaggtatta | 420 |
| gttacctatg | ctgaagtctt | gggaatcaaa | atgcctatta | aggagagtga | tattccccgc | 480 |
| cctaagcaca | ctcctataag | ctatgtgctt | ggacctgtaa | gactcccact | gagtgtgaag | 540 |
| tatccccatc | ctgaatattt | tactgcacaa | ttcagcagac | atcggcagga | gctcttcctc | 600 |
| atcgaagatc | aggcaacctt | ctttccatcc | tcatcaagaa | acagaattgt | gtactatatt | 660 |
| ctctcaagat | gtccttttgg | catagaagat | gggaagaaaa | ggtttgggat | gaaagactg | 720 |
| ctaaactcta | cacttactc | atctgcctat | ccactccatg | atggccaata | ttggaagcca | 780 |
| tcagaacctc | ccaatcctac | caatgaaaga | tacacacttc | accagaattg | ggctcgattt | 840 |
| tcctatttct | acaaggagca | gcctttagac | ttgattaaga | attattatgg | agaaaaaatt | 900 |
| ggtatctatt | ttgtctttct | tggattttac | acagaaatgc | tattctttgc | agctgtagtt | 960 |
| ggcttagctt | gttttatttta | tggcttatta | tcaatggaac | ataacacaag | cagcactgaa | 1020 |
| atctgtgacc | ctgagattgg | tggtcagatg | atcatgtgcc | cactctgtga | tcaagtgtgt | 1080 |
| gattattgga | gactaaatag | tacgtgtttg | gcttcaaagt | tctcccattt | gtttgataat | 1140 |
| gagtcaacag | tgttctttgc | aatattcatg | ggaatttggg | tcaccttatt | tttggagttt | 1200 |
| tggaaacaac | gacaagccag | actggaatat | gaatgggacc | tggtggactt | tgaagaggaa | 1260 |
| cagcagcagc | ttcagctgag | accagaattt | gaagctatgt | gtaaacacag | gaaattgaat | 1320 |
| gcagtgacta | aggagatgga | accttacatg | cctctataca | cgcgtattcc | atggtacttt | 1380 |
| ctttcaggag | ccacagtgac | attatggatg | tctcttgtcg | tcaccagtat | ggtagctgta | 1440 |
| attgtgtacc | gcctgtcagt | ctttgctaca | tttgctagtt | tcatggaaag | tgatgcatcc | 1500 |
| ttaaagcagg | tcaaaagctt | ccttactcct | cagataacca | tcactcac | aggatcatgc | 1560 |
| ttgaacttta | ttgtcatctt | gatcttgaat | ttcttttatg | aaaagatatc | tgcctggatc | 1620 |
| acaaaaatgg | aaattcctcg | aacataccag | gagtatgaga | gcagtcttac | cttgaaaatg | 1680 |
| ttcctgtttc | agtttgtaaa | tttttactca | tcctgcttct | acgtagcttt | ctttaaaggg | 1740 |
| aagttcgtag | gctatcctgg | aaaatacaca | tatttattta | atgagtggag | aagtgaagag | 1800 |
| tgtgatcctg | gaggctgtct | tatagaattg | acaacccaat | tgaccattat | aatgaccggg | 1860 |
| aaacagattt | ttgaaaacat | taagaagcc | atttatccct | tggctttgaa | ttggtggaga | 1920 |
| cgccgaaaag | ctcggacaaa | ctctgagaag | ctgtatagtc | gatgggagca | ggatcatgac | 1980 |
| cttgaaagtt | ttgaccccct | tgggcttttc | tatgagtact | tagaaacagt | tactcaatttt | 2040 |
| ggatttgtta | cactatttgt | ggcctctttt | cctttggctc | ctcttcttgc | tctcataaat | 2100 |

-continued

```
aatattgtag agattcgagt ggatgcctgg aaacttacca ctcaatacag gagaactgta   2160
gcttctaaag ctcatagcat aggtgttggg caagacattc tttatggaat ggctgtcctt   2220
tctgttgcaa ctaatgcctt tattgttgca tttacgtcag acatcattcc ccgtctagtt   2280
tactactatg cttactcaac aaatgccaca cagcctatga caggatatgt gaataatagc   2340
ctgtcagtat tcctgatagc tgattttcca aaccacactg caccttcgga aaaacgagac   2400
ttcatcactt gcaggtacag agattacaga tatcctcctg atgacgagaa taaatatttt   2460
cataatatgc aattctggca tgtccttgct gccaagatga ccttcatcat tgttatggaa   2520
catgttgtgt ttttagttaa atttttgctg gcctggatga tacctgatgt tccaaaagat   2580
gttgtggaga gaatcaagag agaaaagtta atgactatca agattctcca tgattttgag   2640
ctcaacaaat taaagagaaa cttgggaatt aattctaatg aatttgccaa gcatgtcatg   2700
attgaggaaa acaaagcaca gctggctaaa tcaacactc                          2739
```

<210> SEQ ID NO 2
<211> LENGTH: 913
<212> TYPE: PRT
<213> ORGANISM: Homo sapiens

<400> SEQUENCE: 2

```
Met Gly Asp Pro Asp Leu Leu Glu Val Leu Ala Glu Glu Gly Glu Lys
 1               5                  10                  15

Val Asn Lys His Ile Asp Tyr Ser Phe Gln Met Ser Glu Gln Ser Leu
             20                  25                  30

Ser Ser Arg Glu Thr Ser Phe Leu Ile Asn Glu Glu Thr Met Pro Ala
         35                  40                  45

Lys Arg Phe Asn Leu Phe Leu Arg Arg Arg Leu Met Phe Gln Lys Asn
     50                  55                  60

Gln Gln Ser Lys Asp Ser Ile Phe Phe Arg Asp Gly Ile Arg Gln Ile
 65                  70                  75                  80

Asp Phe Val Leu Ser Tyr Val Asp Asp Val Lys Lys Asp Ala Glu Leu
                 85                  90                  95

Lys Ala Glu Arg Arg Lys Glu Phe Glu Thr Asn Leu Arg Lys Thr Gly
            100                 105                 110

Leu Glu Leu Glu Ile Glu Asp Lys Arg Asp Ser Glu Asp Gly Arg Thr
        115                 120                 125

Tyr Phe Val Lys Ile His Ala Pro Trp Glu Val Leu Thr Tyr Ala
    130                 135                 140

Glu Val Leu Gly Ile Lys Met Pro Ile Lys Glu Ser Asp Ile Pro Arg
145                 150                 155                 160

Pro Lys His Thr Pro Ile Ser Tyr Val Leu Gly Pro Val Arg Leu Pro
                165                 170                 175

Leu Ser Val Lys Tyr Pro His Pro Glu Tyr Phe Thr Ala Gln Phe Ser
            180                 185                 190

Arg His Arg Gln Glu Leu Phe Leu Ile Glu Asp Gln Ala Thr Phe Phe
        195                 200                 205

Pro Ser Ser Ser Arg Asn Arg Ile Val Tyr Tyr Ile Leu Ser Arg Cys
    210                 215                 220

Pro Phe Gly Ile Glu Asp Gly Lys Lys Arg Phe Gly Ile Glu Arg Leu
225                 230                 235                 240

Leu Asn Ser Asn Thr Tyr Ser Ser Ala Tyr Pro Leu His Asp Gly Gln
                245                 250                 255
```

-continued

```
Tyr Trp Lys Pro Ser Glu Pro Pro Asn Pro Thr Asn Glu Arg Tyr Thr
            260                 265                 270

Leu His Gln Asn Trp Ala Arg Phe Ser Tyr Phe Tyr Lys Glu Gln Pro
        275                 280                 285

Leu Asp Leu Ile Lys Asn Tyr Tyr Gly Glu Lys Ile Gly Ile Tyr Phe
        290                 295                 300

Val Phe Leu Gly Phe Tyr Thr Glu Met Leu Phe Phe Ala Ala Val Val
305                 310                 315                 320

Gly Leu Ala Cys Phe Ile Tyr Gly Leu Leu Ser Met Glu His Asn Thr
                325                 330                 335

Ser Ser Thr Glu Ile Cys Asp Pro Glu Ile Gly Gly Gln Met Ile Met
            340                 345                 350

Cys Pro Leu Cys Asp Gln Val Cys Asp Tyr Trp Arg Leu Asn Ser Thr
            355                 360                 365

Cys Leu Ala Ser Lys Phe Ser His Leu Phe Asp Asn Glu Ser Thr Val
        370                 375                 380

Phe Phe Ala Ile Phe Met Gly Ile Trp Val Thr Leu Phe Leu Glu Phe
385                 390                 395                 400

Trp Lys Gln Arg Gln Ala Arg Leu Glu Tyr Glu Trp Asp Leu Val Asp
                405                 410                 415

Phe Glu Glu Glu Gln Gln Gln Leu Gln Leu Arg Pro Glu Phe Glu Ala
            420                 425                 430

Met Cys Lys His Arg Lys Leu Asn Ala Val Thr Lys Glu Met Glu Pro
        435                 440                 445

Tyr Met Pro Leu Tyr Thr Arg Ile Pro Trp Tyr Phe Leu Ser Gly Ala
        450                 455                 460

Thr Val Thr Leu Trp Met Ser Leu Val Val Thr Ser Met Val Ala Val
465                 470                 475                 480

Ile Val Tyr Arg Leu Ser Val Phe Ala Thr Phe Ala Ser Phe Met Glu
                485                 490                 495

Ser Asp Ala Ser Leu Lys Gln Val Lys Ser Phe Leu Thr Pro Gln Ile
            500                 505                 510

Thr Thr Ser Leu Thr Gly Ser Cys Leu Asn Phe Ile Val Ile Leu Ile
        515                 520                 525

Leu Asn Phe Phe Tyr Glu Lys Ile Ser Ala Trp Ile Thr Lys Met Glu
        530                 535                 540

Ile Pro Arg Thr Tyr Gln Glu Tyr Glu Ser Ser Leu Thr Leu Lys Met
545                 550                 555                 560

Phe Leu Phe Gln Phe Val Asn Phe Tyr Ser Ser Cys Phe Tyr Val Ala
                565                 570                 575

Phe Phe Lys Gly Lys Phe Val Gly Tyr Pro Gly Lys Tyr Thr Tyr Leu
            580                 585                 590

Phe Asn Glu Trp Arg Ser Glu Glu Cys Asp Pro Gly Gly Cys Leu Ile
        595                 600                 605

Glu Leu Thr Thr Gln Leu Thr Ile Ile Met Thr Gly Lys Gln Ile Phe
        610                 615                 620

Gly Asn Ile Lys Glu Ala Ile Tyr Pro Leu Ala Leu Asn Trp Trp Arg
625                 630                 635                 640

Arg Arg Lys Ala Arg Thr Asn Ser Glu Lys Leu Tyr Ser Arg Trp Glu
                645                 650                 655

Gln Asp His Asp Leu Glu Ser Phe Gly Pro Leu Gly Leu Phe Tyr Glu
            660                 665                 670

Tyr Leu Glu Thr Val Thr Gln Phe Gly Phe Val Thr Leu Phe Val Ala
```

```
                    675                 680                 685

Ser Phe Pro Leu Ala Pro Leu Leu Ala Leu Ile Asn Asn Ile Val Glu
        690                 695                 700

Ile Arg Val Asp Ala Trp Lys Leu Thr Thr Gln Tyr Arg Arg Thr Val
705                 710                 715                 720

Ala Ser Lys Ala His Ser Ile Gly Val Trp Gln Asp Ile Leu Tyr Gly
                725                 730                 735

Met Ala Val Leu Ser Val Ala Thr Asn Ala Phe Ile Val Ala Phe Thr
            740                 745                 750

Ser Asp Ile Ile Pro Arg Leu Val Tyr Tyr Tyr Ala Tyr Ser Thr Asn
                755                 760                 765

Ala Thr Gln Pro Met Thr Gly Tyr Val Asn Asn Ser Leu Ser Val Phe
        770                 775                 780

Leu Ile Ala Asp Phe Pro Asn His Thr Ala Pro Ser Glu Lys Arg Asp
785                 790                 795                 800

Phe Ile Thr Cys Arg Tyr Arg Asp Tyr Arg Tyr Pro Pro Asp Asp Glu
                805                 810                 815

Asn Lys Tyr Phe His Asn Met Gln Phe Trp His Val Leu Ala Ala Lys
            820                 825                 830

Met Thr Phe Ile Ile Val Met Glu His Val Val Phe Leu Val Lys Phe
        835                 840                 845

Leu Leu Ala Trp Met Ile Pro Asp Val Pro Lys Asp Val Val Glu Arg
    850                 855                 860

Ile Lys Arg Glu Lys Leu Met Thr Ile Lys Ile Leu His Asp Phe Glu
865                 870                 875                 880

Leu Asn Lys Leu Lys Glu Asn Leu Gly Ile Asn Ser Asn Glu Phe Ala
                885                 890                 895

Lys His Val Met Ile Glu Glu Asn Lys Ala Gln Leu Ala Lys Ser Thr
            900                 905                 910

Leu

<210> SEQ ID NO 3
<211> LENGTH: 23
<212> TYPE: DNA
<213> ORGANISM: Artificial Sequence
<220> FEATURE:
<223> OTHER INFORMATION: Synthetic primer

<400> SEQUENCE: 3 agtcctttc agcacagtct ttg                                         23

<210> SEQ ID NO 4
<211> LENGTH: 21
<212> TYPE: DNA
<213> ORGANISM: Artificial Sequence
<220> FEATURE:
<223> OTHER INFORMATION: Synthetic primer

<400> SEQUENCE: 4
tgaggcagtg tggagtgagt a                                          21

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
```

-continued

```
gccaatcata tggtctcagt                                        20

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
actgatggcg agctcagacc                                        20

<210> SEQ ID NO 7
<211> LENGTH: 18
<212> TYPE: DNA
<213> ORGANISM: Artificial Sequence
<220> FEATURE:
<223> OTHER INFORMATION: Synthetic primer

<400> SEQUENCE: 7
cctggccgtc aggcagat                                          18

<210> SEQ ID NO 8
<211> LENGTH: 22
<212> TYPE: DNA
<213> ORGANISM: Artificial Sequence
<220> FEATURE:
<223> OTHER INFORMATION: Synthetic primer

<400> SEQUENCE: 8
gacatggaga agatctggca cc                                     22

<210> SEQ ID NO 9
<211> LENGTH: 18
<212> TYPE: DNA
<213> ORGANISM: Artificial Sequence
<220> FEATURE:
<223> OTHER INFORMATION: Synthetic primer

<400> SEQUENCE: 9
ccaacagaat gagaacct                                          18

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10 gacagggtg ggtactttgg                                         20

<210> SEQ ID NO 11
<211> LENGTH: 18
<212> TYPE: DNA
<213> ORGANISM: Artificial Sequence
<220> FEATURE:
<223> OTHER INFORMATION: Synthetic primer

<400> SEQUENCE: 11
cgttggcagc aagatcat                                          18

<210> SEQ ID NO 12
<211> LENGTH: 25
<212> TYPE: DNA
```

<213> ORGANISM: Artificial Sequence
<220> FEATURE:
<223> OTHER INFORMATION: Synthetic primer

<400> SEQUENCE: 12
gggtacctat aatctctgta cctgc                                               25

<210> SEQ ID NO 13
<211> LENGTH: 6661
<212> TYPE: DNA
<213> ORGANISM: Homo sapiens
<300> PUBLICATION INFORMATION:
<308> DATABASE ACCESSION NUMBER: NCBI / NM_213599.2
<309> DATABASE ENTRY DATE: 2015-03-15
<313> RELEVANT RESIDUES IN SEQ ID NO: (1)..(6661)

<400> SEQUENCE: 13
agagcgccca ggagcgctac cggctgaggg tggggaagcg cagggccaag cgcgcgaagc          60
aggttgtggg ggaccgggtc gagtggaagt acccgccgga gaggaaggcc ggctggctgt         120
ggcgcccaga gacggtggag tccgaggagg aggagaagga ggcctgcaga aggaagagca         180
ggcccttaga agtccagcag cagcaactcc ggcggcccac agtcagattc agcacctgcc         240
tcagatctcc acgtctgtct cagctgcccc tctcctgctg cctctcaggc accagtgcca         300
ttaacgagct ggcgaagatg ggcgacccgg atctcctgga agtgttggcg gaggaagggg         360
aaaaagtcaa taagcatata gactactctt tccaaatgag tgagcagagc ctgagcagca         420
gagagaccag ctttctcatc aatgaagaaa caatgcctgc aaagcgattc aatttgttcc         480
tgaggcggcg gcttatgttt caaaaaaatc agcaaagcaa agattctatc ttcttccgag         540
atgggattag gcaaattgat tttgtgcttt cctacgttga tgatgtaaag aaagacgcag         600
agttaaaggc ggaaagaaga aaagagtttg aaactaatct cagaaaaaca ggtcttgagt         660
tggaaataga agacaaaagg gactcggaag atggaagaac ttattttgtc aagatccatg         720
ccccttggga ggtattagtt acctatgctg aagtctgggg aatcaaaatg cctattaagg         780
agagtgatat tccccgccct aagcacactc ctataagcta tgtgcttgga cctgtaagac         840
tcccactgag tgtgaagtat ccccatcctg aatattttac tgcacaattc agcagacatc         900
ggcaggagct cttcctcatc gaagatcagg caaccttctt tccatcctca tcaagaaaca         960
gaattgtgta ctatattctc tcaagatgtc cttttggcat agaagatggg aagaaaaggt        1020
ttgggattga aagactgcta aactctaaca cttactcatc tgcctatcca ctccatgatg        1080
gccaatattg gaagccatca gaacctccca atcctaccaa tgaaagatac acacttcacc        1140
agaattgggc tcgattttcc tatttctaca aggagcagcc tttagacttg attaagaatt        1200
attatgagaa aaaaattggt atctatttttg tctttcttgg attttacaca gaaatgctat        1260
tctttgcagc tgtagttggc ttagcttgtt ttatttatgg cttattatca atggaacata        1320
acacaagcag cactgaaatc tgtgaccctg agattggtgg tcagatgatc atgtgcccac        1380
tctgtgatca agtgtgtgat tattggagac taaatagtac gtgtttggct tcaaagttct        1440
cccatttgtt tgataatgag tcaacagtgt tctttgcaat attcatggga atttgggtca        1500
ccttattttt ggagttttgg aaacaacgac aagccagact ggaatatgaa tgggaccTgg        1560
tggactttga gaggaacag cagcagcttc agctgagacc agaattgaa gctatgtgta        1620 aacacaggaa attgaatgca gtgactaagg agatggaacc ttacatgcct ctatacacgc        1680
gtattccatg gtacttctt tcaggagcca cagtgacatt atggatgtct cttgtcgtca        1740
ccagtatggt agctgtaatt gtgtaccgcc tgtcagtctt tgctacattt gctagtttca        1800

```
tggaaagtga tgcatcctta aagcaggtca aaagcttcct tactcctcag ataaccacat    1860
cactcacagg atcatgcttg aactttattg tcatcttgat cttgaatttc ttttatgaaa    1920
agatatctgc ctggatcaca aaaatggaaa ttcctcgaac ataccaggag tatgagagca    1980
gtcttacctt gaaaatgttc ctgtttcagt ttgtaaattt ttactcatcc tgcttctacg    2040
tagctttctt taaagggaag ttcgtaggct atcctggaaa atacacatat ttatttaatg    2100
agtggagaag tgaagagtgt gatcctggag gctgtcttat agaattgaca acccaattga    2160
ccattataat gaccgggaaa cagattttg gaaacattaa agaagccatt tatcccttgg     2220
ctttgaattg gtggagacgc cgaaaagctc ggacaaactc tgagaagctg tatagtcgat    2280
gggagcagga tcatgacctt gaaagttttg gaccccttgg gcttttctat gagtacttag    2340
aaacagttac tcaatttgga tttgttacac tatttgtggc ctcttttcct ttggctcctc    2400
ttcttgctct cataaataat attgtagaga ttcgagtgga tgcctggaaa cttaccactc    2460
aatacaggag aactgtagct tctaaagctc atagcatagg tgtttggcaa gacattcttt    2520
atggaatggc tgtcctttct gttgcaacta atgcctttat tgttgcattt acgtcagaca    2580
tcattccccg tctagtttac tactatgctt actcaacaaa tgccacacag cctatgacag    2640
gatatgtgaa taatagcctg tcagtattcc tgatagctga ttttccaaac cacactgcac    2700
cttcggaaaa acgagacttc atcacttgca ggtacagaga ttacagatat cctcctgatg    2760
acgagaataa atatttcat aatatgcaat tctggcatgt ccttgctgcc aagatgacct     2820
tcatcattgt tatggaacat gttgtgtttt tagttaaatt tttgctggcc tgatgatac    2880 ctgatgttcc aaaagatgtt gtggagagaa tcaagagaga aaagttaatg actatcaaga    2940
ttctccatga ttttgagctc aacaaattaa aagagaactt gggaattaat tctaatgaat    3000
ttgccaagca tgtcatgatt gaggaaaaca aagcacagct ggctaaatca acactctaat    3060
cagtatagtg aggaagcagc aggtgatctg ccttacttca cttttatcctc tggttttagg    3120 gccagacgcc agaagccatg tgtcaatttt acccttttctt ttttttttttt ttcttttttt   3180 ttttaaactc aaagttttta tacacttta tagaggccaa ctttgtgatg ttggaaatgt     3240
actacttctc tgcttcattg actgggccct ctccagatgt tgttttctga ggtgctgtaa    3300
atgactgttg aaagtgcagg tagaatcaga atactgggaa attatggagt cttgcagttt    3360
agtaagaaac actggccttg gctgtcccca tcactttcca gtgcatctat ttattttgt     3420 ggtcttctct tgggttattt gatacctcct tccccattaa gaaaatgtt ggggcaaaaa     3480 gaaatggatc aaagagactg actgagccct atatatccta tcattttaaa atatgcaaat    3540
gaattgccaa gatcagatga cataagaaaa ctcacacatt aaggtgttaa tgtatcatag    3600
cagaggttta ttcctaacac attcaactac catcagaatc ccagatagtt cttcctggta    3660
aaggcagaat tccttttctc gagactgaaa ttttgggttt caacataaaa caacttggtt    3720
cttagagata taaatttggt tataatagtt tcaagactga tcttatctgg aaagcaacat    3780
tatgaagctg ttagattgct tcaggttctc aagcaaagac acaatacaga agtaaatgtg    3840
ttttcttagt agttaatgga tgcaggacaa tgtatattga ttaatttgtt gattttaatt    3900
tagaaaattg ttaaattatt tcttaaaaat cacttttctt ctggaatgcc aatttcacat    3960
catgaagcct ttttgtataa gttagatacg agttgtttat gataaacatt tctttgcttt    4020
aaaataattg caaatatttt aataagttta caacctttc tattgatgta tcatcttata     4080
caatgctcag tgccttgttc caatacctct gacacacaag aagtcatgtt gttagctagt    4140
```

-continued

```
gatttgatgt gatgtaacat cttaaatgta agcttgtctt aatgaaattg tcagtgtaat    4200
aacaactaca gtcttgaaaa ccaaaagtga atcaaccaac taagaatgag ttcatggact    4260
taataatcta aggggggaaaa aatgtttgtt gaattattcc tctcaaattt aggcttgtgt   4320
tacatgcaca aaaatccttg ttctgttttc acttaaaaaa actaaatatg tataactttg    4380
tgtatacaca cacacacatc tatatatata attattagca ctagagggat atagtccagt    4440
tatgtagtat ttaaatctcc agtttcaaat tataattcac ctccaaaaga atagtttttt    4500
aatcacacac ataagaaatt ttatcacaat atttaaaact aatatttcat tatctaatgc    4560
taataaatta ttgtggtact gccagtatta aatatatggc agatggtatt aactactgat    4620
caatagtaag catacagaac tggggattat ggattttata aactatgaga cagtcacccc    4680
agtttggact gggactaatc cccagtactg atttgtcatc cactgagtag actttatgaa    4740
tattttgggt aatttgaaat gatctcatta ttgaaagatg atttcatatg tagagaagat    4800
aatatttctt tcttgaaaaa acaagtcagg cttaccatga tgtgtgcaac caatgtagga    4860
tctttggctt gtcaaatcag attctccatt gctatagtgt acagtgcaca cagctcatat    4920
tgcttccttc ctgggtgctg ataaaaataa gaaagagcat ggaaattggt ttcttgaata    4980
taagctttaa ttttttaaggc ttaaaagtat tcatagaggt agactgtatg ataaataaaa    5040
acaaatttaa ttcacaaagt tatctgtaca ctgcagtttt aaaatatacc aactaaatta    5100
ttgggtttct ggaagtgaat ggagaaaaca gcaaggaaag aaatcgtttt taagataagt    5160
aaataattcc catggattga taaatatttt ccttttaaaa tgttatggac tgatattttt    5220
tattcacctt taaatttctt atcaagaagt ttatctttgt ttttcagatt taaaaatgaa    5280
atacaggtat tcgtcacttt cctgaaacca tgctaaccaa aatcagtagc caaaccaatt    5340
cagatagatg tgtctcatct aattaaaccc attggttttt atgggagggc tgcattaaga    5400
gcacccaacc accacatgta agttgataat taccagcatg gcaggtgatt ttatctgctg    5460
accaagcgca tagttttgtt ttgttttcag aatgttctag ggaacatttg agattttatg    5520
tgaaataaaa ttttaagtgc caaagccaaa aaaatactta actcttttca aaggccctct    5580
ttcatccttg ccttcgtcaa cttttccttt g cacacaggaa gcaaaatcta cttcaagaca    5640
tttattttag aggaatccat taagaaagga ttgttttact taaatgaaat gctgtcttat    5700
ttttgctgtg tcttttgaca cctcttagct ttaacattct tcttttaacc aagccattat    5760
gcaaagttat caaagaagag gagaaggaaa ggaggacaga tgaaagtgac gggaaatgag    5820
aaagaagagg agtgaggaaa cagttatttc cttatgaatc ctgtgtgttt ctttggaaga    5880
aagagctgtt ccgaggaagt ttggtccagc tgtggttgat aagaggtata tctcttaaaa    5940
aagacaccta atgaaagtga gagaaaagct aaagaaaatt tcaatgtgac cactattatg    6000
tgtcaaaata aaacttagat tccaaagtgg ttttgtagtg ttgggtgcta tgagtaggta    6060
tggatctctg ttgattgact ccagttgaag gtgagaaatc tgtaccaatc attcaaaaag    6120
ggaatctatt gttttgaaag aaactctctc atatttcctt taaattgtta atagttgtta    6180
tgcaactaaa gaatgttatg aagaaaaata gcattgcaaa aagtaccatt ggccagcctt    6240
acaagtcagc cacaatgagt cggtataact actgtgttat tcttttttcta gacaaatttt    6300 gactcttcta cttttatgtg taataattcc agtattctat ttatttcagc attatgtgaa    6360
aaatgataag aatgttaaaa agaaaataat agtgtggttt aattggtatg agataccctgc   6420 ttcctcctcc tcaaaggttt gactgggtgt atctctccta tgtgtgacat tatgtctcct    6480
ggtgttaaca caggaaatga gtgctccttt ttaaaatttc tttcttccaa gttttttttt    6540
```

```
ccaggaagag aaatatgcag ttatgcagga aaagctctct taaataatgt gtacataaat    6600
ctcaagagaa tcaaattcac agagtgaata aagtaataat attaaactac attttgacat    6660
g                                                                    6661
```